US005675060A

United States Patent [19]
Benoist et al.

[11] Patent Number: 5,675,060
[45] Date of Patent: Oct. 7, 1997

[54] TRANSGENIC ARTHRITIC MICE EXPRESSING A T-CELL RECEPTOR TRANSGENE

[75] Inventors: Christophe O. Benoist; Diane J. Mathis, both of Strasbourg, France; Valérie Kouskoff, Denver, Colo.

[73] Assignees: Institut National de la Santé et de la Recherche Médicale; Centre National de la Recherche Scientifique; Université Louis Pasteur, Strasbourg 1, all of Paris, France; E.R. Squibb & Sons, Inc., Princeton, N.J.

[21] Appl. No.: 246,242

[22] Filed: May 19, 1994

[51] Int. Cl.⁶ .................. C12N 5/00; C12P 15/00; A61K 49/00
[52] U.S. Cl. ...................... 800/2; 424/9.2
[58] Field of Search ................... 800/2; 424/9.2

[56] References Cited

U.S. PATENT DOCUMENTS

| | | | |
|---|---|---|---|
| 5,174,986 | 12/1992 | Berns | 424/9 |
| 5,175,383 | 12/1992 | Leder et al. | 800/2 |
| 5,175,384 | 12/1992 | Krimpenfort et al. | 800/2 |

FOREIGN PATENT DOCUMENTS

| | | |
|---|---|---|
| 94/19374 | 9/1994 | European Pat. Off. |
| WO 89/04837 | 6/1989 | WIPO |
| WO 90/06359 | 6/1990 | WIPO |
| WO 92/07070 | 4/1992 | WIPO |

OTHER PUBLICATIONS

Beintema, J.J., "Primary Structures of Pancretic Ribonucleases From *Bovidae*, Impala, Thomson's Gazelle, Nilgai and Water Buffalo," *Biochim. Biophys. Acta* 621:89–103 (1980).
Breukelman, H.J., et al., "Sequences Related to the Ox Pancreatic Ribonuclease Coding Region in the Genomic DNA of Mammalian Species," *J. Mol. Evol.* 37(1):29–35 (Jul. 1993).
Gaastra, W., et al., "The Primary Structure of Giraffe Pancreatic Ribonclease," *FEBS Letters* 41(2):227–232 (May 1974).
Griffiths, M.M., et al., "Collagen–Induced Arthritis and TCRs in SWR and B10.Q Mice Expressing an E$^{k_a}$ Transgene," *J. Immunol.* 153(6):2758–2768 (Sep. 15, 1994).
Kouskoff, V., et al., "Cassette Vectors Directing Expression of T Cell Receptor Genes in Transgenic Mice," *J. Immunol. Meth.* 180(2):273–280 (Mar. 27, 1995).
Natarajan, K., et al., "Major Histocompatibility Complex Determinants Select T–Cell Receptor α Chain Variable Region Dominance in a Peptide–Specific Response," *Proc. Natl. Acad. Sci. USA* 89:8874–8878 (Oct. 1992).
Spinella, D.G., et al., "Receptor Diversity of Insulin–Specific T Cell Lines From C57BL (H–2$^b$) Mice," *J. Immunol.* 138(11):3991–3995 (Jun. 1, 1987).
Berg et al., "Antigen/MHC–Specific T Cells Are Preferentially Exported from the Thymus in the Presence of Their MHC Ligand," *Cell* 58:1035–1046 (1989).

Bevan et al., "Selecting the T Cell Receptor Repertoire," *Science* 264:796–797 (1994).
Blüthmann et al., "T–cell–specific deletion of T–cell receptor transgenes allows functional rearrangement of endogeneous α–and β–genes," *Nature* 334:156–159 (1988).
Borgulya et al., "Exclusion and Inclusion of α and β T Cell Receptor Alleles," *Cell* 69:529–537 (1992).
Candéais et al., "Islet–specific T–cell clones from nononbese diabetic mice express heterogenous T–cell receptors," *PNAS USA* 88:6167–6170 (1991).
Cheng et al., "Protection from Fas–Mediated Apoptosis by s Soluble Form of the Fas Molecule," *Science* 263:1759–1762 (1994).
Chiocchia et al., "T Cell Regulation of Collagen–Induced Arthritis in Mice," *J. Immunol.* 145(2):519–525 (1990).
Christian and Paget, "Rheumatoid Arthritis" Chapter 63, in: *Immunological Diseases*, vol. II, 3rd Ed. Samter, M., ed., Little, Brown and Co., pp. 1061–1076 (1978).
Davis and Bjorkman, "T–cell antigen receptor genes and T–cell recognition," *Nature* 334(4):395–402 (1988).
Dellabona et al., "A single amino acid substitution in the A$^k$ molecule fortuitously provokes an alloresponse," *Eur. J. Immunol.* 21:209–213 (1991).
Firestein and Zvaifler, "How Important Are T Cells In Chroni Rheumatoid Synovitis?," *Arthritis and Rheumatism* 33(6):768–773 (1990).
Janeway, C.A., "How the Immune System Recognizes Invaders," *Sci. American* 269(3):72–79 (1993).
Jasin et al., "Immunologic models used for the study of rheumatoid arthritis," *Fed. Proc. (USA)* 32(2):147–152 (1973).

(List continued on next page.)

*Primary Examiner*—Deborah Crouch
*Attorney, Agent, or Firm*—Sterne, Kessler, Goldstein & Fox, P.L.L.C.

[57] ABSTRACT

A transgenic animal model for arthritis is disclosed. The arthritic condition results from genetic (or immunologic) manipulations that result in the T cell receptor (TCR) repertoire of the animal being substantially limited relative to the TCR repertoire of a wildtype control animal. The TCR repertoire of the arthritic animal, albeit limited, is functionally viable. In a preferred embodiment, the invention relates to transgenic arthritic mice wherein arthritis results from (1) a transgenic allele which encodes and expresses TCR α and β subunits that combine in T lymphocytes of the transgenic animal to form a TCR that recognizes an antigen comprising one or more epitopes of an oligopeptide derived from amino acids 41–61 of bovine pancreatic ribonuclease and/or (2) polypeptide arthritogenic self antigens derived from endogenous proteins. The transgenic arthritic mice of the invention provides an animal model which faithfully mimics rheumatoid arthritis and by which human arthritogenic and therapeutic anti-arthritic compositions are evaluated. Also provided herein are therapeutic oligopeptides derived from the variable regions of the TCRs of the transgenes of the invention and/or from the amino acid sequence of proteins comprising endogenous polypeptide arthritogenic antigens.

17 Claims, 9 Drawing Sheets

OTHER PUBLICATIONS

Kartz et al., "Following a Diabetogenic T Cell from Genesis through Pathogenesis," *Cell* 74:1089–1100 (1993).

Krimpenfort et al., "Transcription of T cell receptor β–chain genes is controlled by a downstream regulatory element," *EMBO J.* 7(3):745–750 (1988).

Lanchbury and Pitzalis, "Cellular immune mechanisms in rheumatoid arthritis and other inflammatory arthritides," *Current Opinion Immunology* 5:918–924 (1993).

Lee and Sarvetnick, "Transgenes in autoimmunity," *Current Opinion Immunology* 4:723–727 (1992).

Mori et al., "Expression of a Transgenic T Cell Receptor β Chain Enhances Collagen–induced Arthritis," *J. Exp. Med.* 176:381–388 (1992).

Peccoud et al., "Delineation of antigen contact residues on an MHC class II molecule," *EMBO J.* 9(13):4215–4223.

Rhein, R., "RAC approves first gene–transfer trial for rheumatoid arthritis," *Biotechnology Newswatch* pp. 1,3–4 (Jun. 20, 1994).

Rhein, R., "TNF–blockade effective in treating rheumatoid arthritis," *Biotechnology Newswatch* pp. 4–5, (Nov. 7, 1994).

Schwartz, R.S., "Autoimmunity and Autoimmune Diseases," Chapter 30, in: *Fundamental Immunology*, 3rd Ed., Paul, W.E., ed., Raven Press, NY, pp. 1033–1097 (1993).

Steinman, L., "Autoimmune Disease," *Sci. American* 269(3):106–114 (1993).

Steinmetz et al., "Transgenic mice to study T–cell receptor gene regulation and repertoire formation," *Genome* 31:652–655 (1989).

Teh et al., "Thymic major histocompatibility complex antigens and the αβ T–cell receptor determine the CD4/CD8 phenotype of T cells," *Nature* 335:229–233 (1988).

Uematsu, Y., "Preferential association of α and β chains of the T cell antigen receptor," *Eur. J. Immunol.* 22:603–606 (1992).

Uematsu et al., "In Transgenic Mice the Introduced Functional T cell Receptor β Gene Prevents Expression of Endogenous β Genes," *Cell* 52:831–841 (1988).

Watson et al., "Human HLA–DRβ Gene Hypervariable Region Homology in the BioBreeding BB Rat: Selection of the Diabetic–resistant Subline as a Rheumatoid Arthritis Research Tool to Characterize the Immunopathologic Response to Human Type II Collagen," *J. Exp. Med.* 172:1331–1339 (1990).

Watson et al., "The Introduction of Foreign Genes Into Mice," Chapter 14, in: *Recombinant DNA*, 2nd ed., W.H. Freeman & Co., NY, pp. 255–272 (1992).

Weissman and Cooper, "How the Immune System Develops," *Sci. American* 269(3):64–71 (1993).

Wordsworth, P., "Rheumatoid Arthritis," *Current Opinion Immunology* 4(6):766–769 (1992).

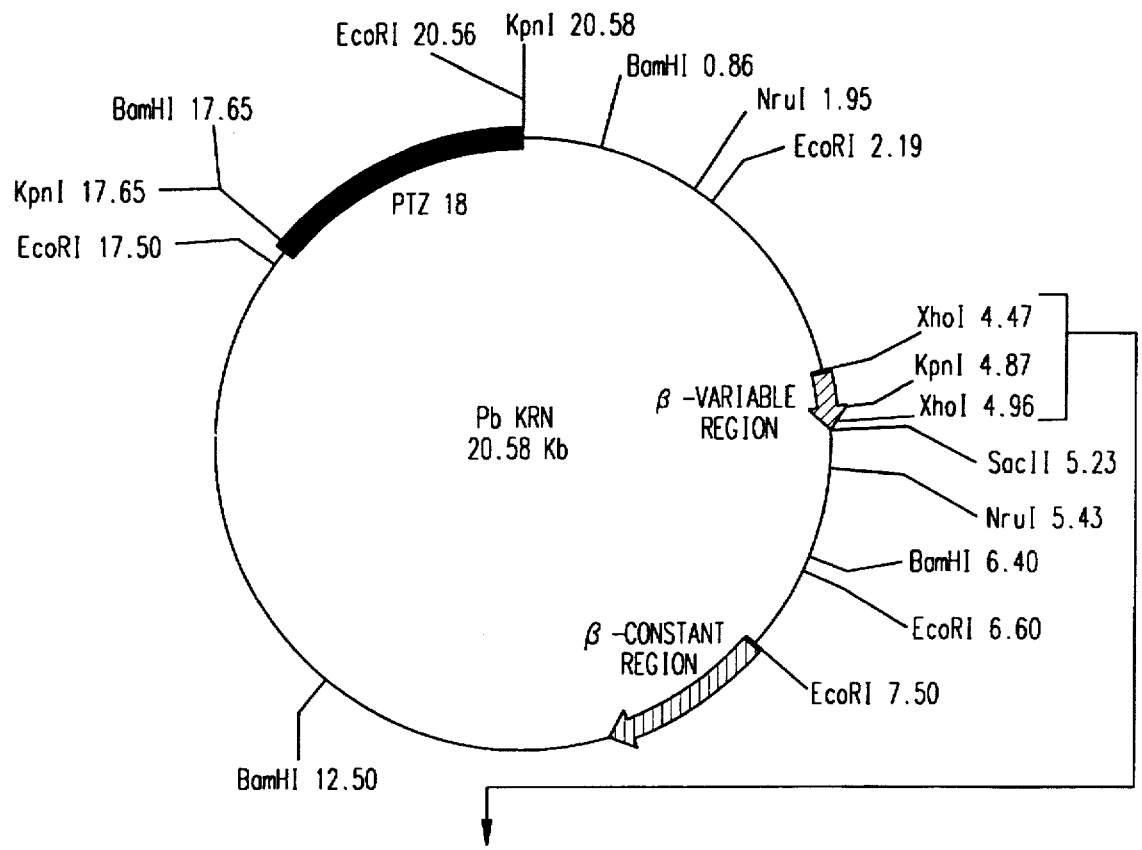

```
            10         20         30         40         50         60
    Xho I    |          |          |          |          |          |
 1  CTCGAGCCAA AGTATGAACA AGTGGGTTTT CTGCTGGGTA ACCCTTTGTC TCCTTACTGT   leader

61  ACGTAAGGCT CTGGGCTCTC TGGGTTCCTG TTGCCGAGTG CACATCTTAA CCCCCCTGCC

121 CTGGGTAGCA GTGCCAAACC CCTTCCAGAC TGATTCTTTT TCTTTTCCAG AGACCACACA   Vβ6

181 TGGTGATGGT GGCATCATTA CTCAGACACC CAAATTCCTG ATTGGTCAGG AAGGGCAAAA

241 ACTGACCTTG AAATGTCAAC AGAATTTCAA TCATGATACA ATGTACTGGT ACCGACAGGA
                                                            Kpn I
301 TTCAGGGAAA GGATTGAGAC TGATCTACTA TTCAATAACT GAAAACGCCG ATCTATCTGA

361 AGGCTATGAT GCGTCTCGAG AGAAGAAGTC ATCTTTTTCT CTCACTGTGA CATCTGCCCA
                 Xho I
421 GAAGAACGAG ATGGCCCTTT TTCTCTGTGC CAGCAGTATA TCCACAAACA ACCAGGCTCC

481 GCTTTTTGGA GAGGGACTC GACTCTCTGT TCTAGGTAAA CTATGGGACC AAACTGGTGG    Jβ1.5

541 GACCATTGTC CTTTGGACCT GGAGTGTCTC TGTAACCCCG CGG
                                          Sac II
```

FIG.1B

SEQUENCE LISTING ( 1 ) GENERAL INFORMATION:

( i i i ) NUMBER OF SEQUENCES: 9

( 2 ) INFORMATION FOR SEQ ID NO:1:

( i ) SEQUENCE CHARACTERISTICS:
        ( A ) LENGTH: 21 amino acids
        ( B ) TYPE: amino acid
        ( D ) TOPOLOGY: unknown ( i i ) MOLECULE TYPE: protein ( x i ) SEQUENCE DESCRIPTION: SEQ ID NO:1:

```
Lys  Pro  Val  Asn  Thr  Phe  Val  His  Glu  Ser  Leu  Ala  Asp  Val  Gln  Ala
1                   5                        10                       15
Val  Cys  Ser  Gln  Lys
               20
```

( 2 ) INFORMATION FOR SEQ ID NO:2:

( i ) SEQUENCE CHARACTERISTICS:
        ( A ) LENGTH: 721 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:2:

```
CCCGGGAGAA  TACCACTCTG  AAGATGAACA  CTTCTCCAGT  TTTAGTGACT  GCGATGCTGC    60
TGTTCATGCT  TGGTAAGTT   AGCGACTTAC  CACTCTCTCT  TTCTTCTATA  ATGTTAGAAT   120
ATATTTAATC  TATGAAATTT  GTCCTTGCTA  TAACACAGAT  ATCCTCTTCT  TCCTCCAGGG   180
ATGAGAAAGA  CCCACGGAGG  TTCAGTGACC  CAGAAACAAG  GTCAAGTGAC  CCTTTCAGAA   240
GATGACTTCC  TATTTATAAA  TTGCACTTAT  TCTACCACAA  CGTACCCAAC  TCTTTTCTGG   300
TATGTCCAAT  ATCCTGGACA  AGGTCCACAG  CTCCTTCTGA  AAGTCACAAC  TGCCAACAAC   360
AAGGGAATCA  GCAGAGGCTT  TGAAGCTACA  TATGAGAAAG  GGACCACGTC  CTTCCACTTA   420
CAGAAAGCCT  CAGTGCAGGA  GTCAGACTCA  GCCGTGTACT  TCTGTGCTCT  GGCCCCTTCC   480
AATACCAACA  AAGTCGTCTT  TGGAACAGGG  ACCAGATTAC  AAGTATTACC  AAGTAAGTTC   540
TGAGACAGTG  AAGCAATTTG  AAAAGGTGTT  TTCTATAAAT  TCCAGCTTTG  GCTGGATGTC   600
CAGGCCGCCC  TTCCTAGCAC  TGCATTCATT  CTGCAGCTAC  CCTCCATGCC  TCTAGCTGTT   660
```

```
GTGTCCATGG GAGAGCAGGG TGTCATTTCC CAGGTTAACC TTCTGTAAAC GCGGCCGCTT      720
A                                                                      721
```

( 2 ) INFORMATION FOR SEQ ID NO:3:

( i ) SEQUENCE CHARACTERISTICS:
        ( A ) LENGTH: 583 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:3:

```
CTCGAGCCAA AGTATGAACA AGTGGGTTTT CTGCTGGGTA ACCCTTGTC TCCTTACTGT        60
AGGTAAGGCT CTGGGCTCTC TGGGTTCCTG TTGCCGAGTG CACATCTTAA CCCCCCTGCC      120
CTGGGTAGCA GTGCCAAACC CCTTCCAGAC TGATTCTTTT TCTTTTCCAG AGACCACACA      180
TGGTGATGGT GGCATCATTA CTCAGACACC CAAATTCCTG ATTGGTCAGG AAGGGCAAAA      240
ACTGACCTTG AAATGTCAAC AGAATTTCAA TCATGATACA ATGTACTGGT ACCGACAGGA      300
TTCAGGGAAA GGATTGAGAC TGATCTACTA TTCAATAACT GAAAACGGCG ATCTATCTGA      360
AGGCTATGAT GCGTCTCGAG AGAAGAAGTC ATCTTTTCT CTCACTGTGA CATCTGCCCA       420
GAAGAACGAG ATGGCCCTTT TTCTCTGTGC CAGCAGTATA TCCACAAACA ACCAGGCTCC      480
GCTTTTTGGA GAGGGACTC GACTCTCTGT TCTAGGTAAA CTATGGGACC AAACTGGTGG       540
GACCATTGTC CTTTGGACCT GGAGTGTCTC TGTAACCCCG CGG                        583
```

( 2 ) INFORMATION FOR SEQ ID NO:4:

( i ) SEQUENCE CHARACTERISTICS:
        ( A ) LENGTH: 403 base pairs
        ( B ) TYPE: nucleic acid
        ( C ) STRANDEDNESS: unknown
        ( D ) TOPOLOGY: unknown ( i i ) MOLECULE TYPE: DNA (genomic)

( i x ) FEATURE:
        ( A ) NAME/KEY: CDS
        ( B ) LOCATION: 1..403

( x i ) SEQUENCE DESCRIPTION: SEQ ID NO:4:

```
ATG  AAC  ACT  TCT  CCA  GTT  TTA  GTG  ACT  GCG  ATG  CTG  CTG  TTC  ATG  CTT      48
Met  Asn  Thr  Ser  Pro  Val  Leu  Val  Thr  Ala  Met  Leu  Leu  Phe  Met  Leu
 1                    5                        10                       15

GGG  ATG  AGA  AAG  ACC  CAC  GGA  GGT  TCA  GTG  ACC  CAG  AAA  CAA  GGT  CAA      96
Gly  Met  Arg  Lys  Thr  His  Gly  Gly  Ser  Val  Thr  Gln  Lys  Gln  Gly  Gln
                20                   25                        30

GTG  ACC  CTT  TCA  GAA  GAT  GAC  TTC  CTA  TTT  ATA  AAT  TGC  ACT  TAT  TCT     144
Val  Thr  Leu  Ser  Glu  Asp  Asp  Phe  Leu  Phe  Ile  Asn  Cys  Thr  Tyr  Ser
               35                        40                    45

ACC  ACA  ACG  TAC  CCA  ACT  CTT  TTC  TGG  TAT  GTC  CAA  TAT  CCT  GGA  CAA     192
Thr  Thr  Thr  Tyr  Pro  Thr  Leu  Phe  Trp  Tyr  Val  Gln  Tyr  Pro  Gly  Gln
          50                        55                   60

GGT  CCA  CAG  CTC  CTT  CTG  AAA  GTC  ACA  ACT  GCC  AAC  AAC  AAG  GGA  ATC     240
Gly  Pro  Gln  Leu  Leu  Leu  Lys  Val  Thr  Thr  Ala  Asn  Asn  Lys  Gly  Ile
 65                        70                   75                        80

AGC  AGA  GGC  TTT  GAA  GCT  ACA  TAT  GAG  AAA  GGG  ACC  ACG  TCC  TTC  CAC     288
Ser  Arg  Gly  Phe  Glu  Ala  Thr  Tyr  Glu  Lys  Gly  Thr  Thr  Ser  Phe  His
                    85                        90                   95

TTA  CAG  AAA  GCC  TCA  GTG  CAG  GAG  TCA  GAC  TCA  GCC  GTG  TAC  TTC  TGT     336
```

| Leu | Gln | Lys | Ala | Ser | Val | Gln | Glu | Ser | Asp | Ser | Ala | Val | Tyr | Phe | Cys | |
|---|---|---|---|---|---|---|---|---|---|---|---|---|---|---|---|---|
| | | | 100 | | | | 105 | | | | | 110 | | | | |

| GCT | CTG | GCC | CCT | TCC | AAT | ACC | AAC | AAA | GTC | GTC | TTT | GGA | ACA | GGG | ACC | 384 |
|---|---|---|---|---|---|---|---|---|---|---|---|---|---|---|---|---|
| Ala | Leu | Ala | Pro | Ser | Asn | Thr | Asn | Lys | Val | Val | Phe | Gly | Thr | Gly | Thr | |
| | | 115 | | | | | 120 | | | | | 125 | | | | |

| AGA | TTA | CAA | GTA | TTA | CCA | A | 403 |
|---|---|---|---|---|---|---|---|
| Arg | Leu | Gln | Val | Leu | Pro | | |
| | 130 | | | | | | |

( 2 ) INFORMATION FOR SEQ ID NO:5:

( i ) SEQUENCE CHARACTERISTICS:
        ( A ) LENGTH: 134 amino acids
        ( B ) TYPE: amino acid
        ( D ) TOPOLOGY: linear ( i i ) MOLECULE TYPE: protein ( x i ) SEQUENCE DESCRIPTION: SEQ ID NO:5:

| Met | Asn | Thr | Ser | Pro | Val | Leu | Val | Thr | Ala | Met | Leu | Leu | Phe | Met | Leu |
|---|---|---|---|---|---|---|---|---|---|---|---|---|---|---|---|
| 1 | | | | 5 | | | | | 10 | | | | | 15 | |

| Gly | Met | Arg | Lys | Thr | His | Gly | Gly | Ser | Val | Thr | Gln | Lys | Gln | Gly | Gln |
|---|---|---|---|---|---|---|---|---|---|---|---|---|---|---|---|
| | | | 20 | | | | | 25 | | | | | 30 | | |

| Val | Thr | Leu | Ser | Glu | Asp | Asp | Phe | Leu | Phe | Ile | Asn | Cys | Thr | Tyr | Ser |
|---|---|---|---|---|---|---|---|---|---|---|---|---|---|---|---|
| | | 35 | | | | | 40 | | | | | 45 | | | |

| Thr | Thr | Thr | Tyr | Pro | Thr | Leu | Phe | Trp | Tyr | Val | Gln | Tyr | Pro | Gly | Gln |
|---|---|---|---|---|---|---|---|---|---|---|---|---|---|---|---|
| | 50 | | | | | 55 | | | | | 60 | | | | |

| Gly | Pro | Gln | Leu | Leu | Leu | Lys | Val | Thr | Thr | Ala | Asn | Asn | Lys | Gly | Ile |
|---|---|---|---|---|---|---|---|---|---|---|---|---|---|---|---|
| 65 | | | | | 70 | | | | | 75 | | | | | 80 |

| Ser | Arg | Gly | Phe | Glu | Ala | Thr | Tyr | Glu | Lys | Gly | Thr | Thr | Ser | Phe | His |
|---|---|---|---|---|---|---|---|---|---|---|---|---|---|---|---|
| | | | | 85 | | | | | 90 | | | | | 95 | |

| Leu | Gln | Lys | Ala | Ser | Val | Gln | Glu | Ser | Asp | Ser | Ala | Val | Tyr | Phe | Cys |
|---|---|---|---|---|---|---|---|---|---|---|---|---|---|---|---|
| | | | 100 | | | | 105 | | | | | 110 | | | |

| Ala | Leu | Ala | Pro | Ser | Asn | Thr | Asn | Lys | Val | Val | Phe | Gly | Thr | Gly | Thr |
|---|---|---|---|---|---|---|---|---|---|---|---|---|---|---|---|
| | | 115 | | | | | 120 | | | | | 125 | | | |

| Arg | Leu | Gln | Val | Leu | Pro |
|---|---|---|---|---|---|
| | 130 | | | | |

( 2 ) INFORMATION FOR SEQ ID NO:6:

( i ) SEQUENCE CHARACTERISTICS:
        ( A ) LENGTH: 462 base pairs
        ( B ) TYPE: nucleic acid
        ( C ) STRANDEDNESS: unknown
        ( D ) TOPOLOGY: unknown ( i i ) MOLECULE TYPE: DNA (genomic)

( i x ) FEATURE:
        ( A ) NAME/KEY: CDS
        ( B ) LOCATION: 1..462
        ( D ) OTHER INFORMATION: /label=peptide ( x i ) SEQUENCE DESCRIPTION: SEQ ID NO:6:

| ATG | AAC | AAG | TGG | GTT | TTC | TGC | TGG | GTA | ACC | CTT | TGT | CTC | CTT | ACT | GTA | 48 |
|---|---|---|---|---|---|---|---|---|---|---|---|---|---|---|---|---|
| Met | Asn | Lys | Trp | Val | Phe | Cys | Trp | Val | Thr | Leu | Cys | Leu | Leu | Thr | Val | |
| 1 | | | | 5 | | | | | 10 | | | | | 15 | | |

| GAG | ACC | ACA | CAT | GGT | GAT | GGT | GGC | ATC | ATT | ACT | CAG | ACA | CCC | AAA | TTC | 96 |
|---|---|---|---|---|---|---|---|---|---|---|---|---|---|---|---|---|
| Glu | Thr | Thr | His | Gly | Asp | Gly | Gly | Ile | Ile | Thr | Gln | Thr | Pro | Lys | Phe | |
| | | | 20 | | | | | 25 | | | | | 30 | | | |

| CTG | ATT | GGT | CAG | GAA | GGG | CAA | AAA | CTG | ACC | TTG | AAA | TGT | CAA | CAG | AAT | 144 |
|---|---|---|---|---|---|---|---|---|---|---|---|---|---|---|---|---|
| Leu | Ile | Gly | Gln | Glu | Gly | Gln | Lys | Leu | Thr | Leu | Lys | Cys | Gln | Gln | Asn | |
| | | 35 | | | | | 40 | | | | | 45 | | | | |

| | | | | | | | | | | | | | | | | |
|---|---|---|---|---|---|---|---|---|---|---|---|---|---|---|---|---|
| TTC | AAT | CAT | GAT | ACA | ATG | TAC | TGG | TAC | CGA | CAG | GAT | TCA | GGG | AAA | GGA | 192 |
| Phe | Asn | His | Asp | Thr | Met | Tyr | Trp | Tyr | Arg | Gln | Asp | Ser | Gly | Lys | Gly | |
| | 50 | | | | 55 | | | | | 60 | | | | | | |
| TTG | AGA | CTG | ATC | TAC | TAT | TCA | ATA | ACT | GAA | AAC | GGC | GAT | CTA | TCT | GAA | 240 |
| Leu | Arg | Leu | Ile | Tyr | Tyr | Ser | Ile | Thr | Glu | Asn | Gly | Asp | Leu | Ser | Glu | |
| 65 | | | | | 70 | | | | 75 | | | | | | 80 | |
| GGC | TAT | GAT | GCG | TCT | CGA | GAG | AAG | AAG | TCA | TCT | TTT | TCT | CTC | ACT | GTG | 288 |
| Gly | Tyr | Asp | Ala | Ser | Arg | Glu | Lys | Lys | Ser | Ser | Phe | Ser | Leu | Thr | Val | |
| | | | | 85 | | | | | 90 | | | | | 95 | | |
| ACA | TCT | GCC | CAG | AAG | AAC | GAG | ATG | GCC | CTT | TTT | CTC | TGT | GCC | AGC | AGT | 336 |
| Thr | Ser | Ala | Gln | Lys | Asn | Glu | Met | Ala | Leu | Phe | Leu | Cys | Ala | Ser | Ser | |
| | | | 100 | | | | | 105 | | | | | 110 | | | |
| ATA | TCC | ACA | AAC | AAC | CAG | GCT | CCG | CTT | TTT | GGA | GAG | GGG | ACT | CGA | CTC | 384 |
| Ile | Ser | Thr | Asn | Asn | Gln | Ala | Pro | Leu | Phe | Gly | Glu | Gly | Thr | Arg | Leu | |
| | | 115 | | | | | 120 | | | | | 125 | | | | |
| TCT | GTT | CTA | GGT | AAA | CTA | TGG | GAC | CAA | ACT | GGT | GGG | ACC | ATT | GTC | CTT | 432 |
| Ser | Val | Leu | Gly | Lys | Leu | Trp | Asp | Gln | Thr | Gly | Gly | Thr | Ile | Val | Leu | |
| | 130 | | | | | 135 | | | | | 140 | | | | | |
| TGG | ACC | TGG | AGT | GTC | TCT | GTA | ACC | CCG | CGG | | | | | | | 462 |
| Trp | Thr | Trp | Ser | Val | Ser | Val | Thr | Pro | Arg | | | | | | | |
| 145 | | | | | 150 | | | | | | | | | | | |

( 2 ) INFORMATION FOR SEQ ID NO:7:

( i ) SEQUENCE CHARACTERISTICS:
        ( A ) LENGTH: 154 amino acids
        ( B ) TYPE: amino acid
        ( D ) TOPOLOGY: linear ( i i ) MOLECULE TYPE: protein ( x i ) SEQUENCE DESCRIPTION: SEQ ID NO:7:

| | | | | | | | | | | | | | | | |
|---|---|---|---|---|---|---|---|---|---|---|---|---|---|---|---|
| Met | Asn | Lys | Trp | Val | Phe | Cys | Trp | Val | Thr | Leu | Cys | Leu | Leu | Thr | Val |
| 1 | | | | 5 | | | | | 10 | | | | | 15 | |
| Glu | Thr | Thr | His | Gly | Asp | Gly | Gly | Ile | Ile | Thr | Gln | Thr | Pro | Lys | Phe |
| | | | 20 | | | | | 25 | | | | | 30 | | |
| Leu | Ile | Gly | Gln | Glu | Gly | Gln | Lys | Leu | Thr | Leu | Lys | Cys | Gln | Gln | Asn |
| | | | 35 | | | | | 40 | | | | 45 | | | |
| Phe | Asn | His | Asp | Thr | Met | Tyr | Trp | Tyr | Arg | Gln | Asp | Ser | Gly | Lys | Gly |
| | 50 | | | | 55 | | | | | 60 | | | | | |
| Leu | Arg | Leu | Ile | Tyr | Tyr | Ser | Ile | Thr | Glu | Asn | Gly | Asp | Leu | Ser | Glu |
| 65 | | | | | 70 | | | | 75 | | | | | | 80 |
| Gly | Tyr | Asp | Ala | Ser | Arg | Glu | Lys | Lys | Ser | Ser | Phe | Ser | Leu | Thr | Val |
| | | | | 85 | | | | | 90 | | | | | 95 | |
| Thr | Ser | Ala | Gln | Lys | Asn | Glu | Met | Ala | Leu | Phe | Leu | Cys | Ala | Ser | Ser |
| | | | 100 | | | | | 105 | | | | | 110 | | |
| Ile | Ser | Thr | Asn | Asn | Gln | Ala | Pro | Leu | Phe | Gly | Glu | Gly | Thr | Arg | Leu |
| | | 115 | | | | | 120 | | | | | 125 | | | |
| Ser | Val | Leu | Gly | Lys | Leu | Trp | Asp | Gln | Thr | Gly | Gly | Thr | Ile | Val | Leu |
| | 130 | | | | | 135 | | | | | 140 | | | | |
| Trp | Thr | Trp | Ser | Val | Ser | Val | Thr | Pro | Arg | | | | | | |
| 145 | | | | | 150 | | | | | | | | | | |

( 2 ) INFORMATION FOR SEQ ID NO:8:

( i ) SEQUENCE CHARACTERISTICS:
        ( A ) LENGTH: 40 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:8:

TTTGTTGGTA TTGGAAGGGG CCAGAGCACA GAAGTACACG    40

( 2 ) INFORMATION FOR SEQ ID NO:9:

( i ) SEQUENCE CHARACTERISTICS:
 ( A ) LENGTH: 26 amino acids
 ( B ) TYPE: amino acid
 ( C ) STRANDEDNESS: unknown
 ( D ) TOPOLOGY: unknown ( i i ) MOLECULE TYPE: protein ( x i ) SEQUENCE DESCRIPTION: SEQ ID NO:9:

```
Pro Thr Gly Pro Leu Gly Pro Lys Gly Gln Thr Gly Glu Leu Gly Ile
1               5               10                  15

Ala Gly Phe Lys Gly Glu Gln Gly Pro Lys
            20                  25
```

TRANSGENIC ARTHRITIC MICE EXPRESSING A T-CELL RECEPTOR TRANSGENE

FIELD OF THE INVENTION

The present invention relates to transgenic non-human animals that have been genetically engineered to develop arthritis and thus provides animal models for human arthritic diseases such as Rheumatoid Arthritis. More particularly, the invention relates to transgenic animals wherein the T cell receptor (TCR) populations of the transgenic animals consist substantially of copies of a TCR that (a) comprises transgene encoded TCRα and TCP-β subunits and (b) directs T cells to react with self antigens in the transgenic animals. Most particularly, the invention relates to transgenic animals wherein a limited TCR repertoire, consisting substantially of transgene encoded TCRs, acts during development of the transgenic animal to initiate a cascade of events that culminates in the transgenic animal developing severe arthritic symptoms in a reproducible and thus predictable manner.

BACKGROUND OF THE INVENTION

Animals have a complex array of molecular and cellular defenses, collectively referred to as the immune system, that recognize and attack potentially harmful foreign or endogenous but abnormal cells (respectively represented by, e.g., pathogens such as bacteria or viruses, and cancerous or pathogen-infected cells), but that do not attack but rather tolerate endogenous normal cells. When stimulated by foreign or abnormal biomolecules, the immune system undergoes a series of activities designed to neutralize and destroy the pathogens, or cancerous or pathogen-infected cells, with which the foreign or abnormal biomolecules are associated. These activities, collectively known as an immune response, may consist of a cell-mediated immune response, a humoral (antibody-mediated) immune response, or an immune response that includes elements of cell-mediated and humoral responses.

Humoral immune responses are mediated by antibodies, glycoproteins that bind specific foreign or abnormal biomolecules and attract other components of the immune system thereto. Antibodies are immunoglobulin (Ig) molecules produced by B cells, lymphocytes which originate in avian bursa or in mammalian bone marrow but migrate to and mature in other organs, particularly the spleen. Robertson, M., Nature 301: 114 (1983). Cell-mediated immune responses are the result of activities of T cells, lymphocytes that undergo maturation within the thymus of an animal. Tizard, p. 163.

T cell activities vary considerably among different subpopulations of T cells within an animal. Cytotoxic T cells recognize and destroy foreign cells (graft rejection) or endogenous but abnormal cells (e.g., cancerous cells or cells infected with intercellular parasites such as viruses and bacteria). Helper T cells interact with, and produce biomolecules that influence the behavior of, both B cells and cytotoxic T cells, in order to promote and direct antibody production and cytotoxic activities, respectively. Mosier, D. E., Science 158: 1573–1575 (1967). Other classes of T cells, including suppressor T cells and memory T cells, also exist. Miedema, F., and Melief, C. J. M., Immunol. Today 6: 258–259 (1983); Tizard, I. R., Immunology: An Introduction, Saunders, Philadelphia (1988), pp. 225–228. Classes of T cells are to some extent distinguished on the basis that different T cells display different CD proteins on their surfaces. Immature T cells display both CD4 and CD8 proteins (i.e., immature T cells are $CD4^+8^+$), mature helper T cells are $CD4^+8^-$ (i.e., display CD4 protein but not CD8 protein) and mature cytotoxic T cells are $CD4^-8^+$ (i.e., display CD8 protein but not CD4 protein). Smith, L., Nature 326: 798–800 (1987); Weissman, I. L., and Cooper, M. D., Sci. American 269: 65–71 (1993).

In order to function properly, the T and B cells of an animal's immune system must accurately and reliably identify an enormous number of non-self compositions that is foreign or endogenous but abnormal compositions. Recognition and identification by the immune system occurs at the molecular level. An antigen, a molecular composition having the potential to generate an immune response, is composed of one or more molecular-sized identifying features known as epitopes. A polypeptide antigen which has an amino acid sequence which comprises, e.g., a hundred amino acids might comprise dozens of epitopes, wherein each epitope is defined by a portion of the polypeptide comprising from about 3 to about 15 amino acids. The number of eptitopes derivable from polypeptides alone is estimated to be about ten million. Tizard, p. 25.

An antigen encountered by a T or B cell of an animal must be identified as either being associated with normal endogenous (i.e., self) antigens, an immune response to which would be injurious to the animal, or with foreign or abnormal (i.e., non-self) antigens, to which an immune response should be mounted. The process can be analogized to "friend or foe" identification in human combat. If the immune system fails to identify antigens associated with invading pathogens or tumor cells as non-self, then these "enemies" can slip through the system's defenses. If the immune system mistakenly identifies an animal's endogenous antigens as non-self, then the parts of the animal's body that comprise the endogenous antigens will face "friendly fire" from the immune system. The latter situation, in which an animal's immune system mistakenly wages cellular and molecular "war" against another, normal part of an animal's body, is known generally as "autoimmune disease."

As part of the immune system's means of identifying antigens, individual T and B cells produce antigen receptors which are displayed on the T or B cell's surface and which bind specific antigens. The T cell receptors (TCRs) produced by and displayed on an individual T cell comprise heavy (TCRβ) and light (TCRα) polypeptide subunits. Each TCR α and β subunit has a carboxy-terminal constant region, the amino acid sequence of which does not vary from T cell to T cell, and an amino-terminal variable region, the amino acid sequence of which does vary from T cell to T cell. When TCRα and TCRβ subunits associate with each other, the variable regions of the TCRα and TCRβ polypeptide subunits combine to form the unique antigen-binding portion of the TCR. Davis, M. M., and Bjorkman, P. J., Nature 334: 395–404 (1988). Similarly, individual B cells produce and display antigen receptors that comprise Ig molecules which have unique antigen-binding portions due to unique amino acid sequences in the variable regions of each of the two antibody subunits, known as the Ig heavy and Ig light chains. Each B cell membrane comprises from 20,000 to 200,000 identical Ig molecules. Tizard, pp. 78–80 and 202.

Although each individual T or B cell displays identical antigen receptors, an animal's collection of different antigen receptors is quite diverse. The variable region of an Ig heavy chain, or that of a TCRβ chain, is encoded by three gene segments, the variable (V), diversity (D) and joining (J) segments. The variable region of an Ig light chain, or that of a TCRα chain, is encoded by V and J gene segments. Multiple DNA sequences encoding many different V, D and I gene segments are present as unexpressed copies in germline DNA; an analogous but different collection of variable gene segments for TCR subunits is also present. During development of an animal, genes encoding diverse variable regions are generated in individual cells of the immune system by the random joining of V, D and J, or V and J, gene segments. The process of DNA rearrangements that generates a randomly assembled variable region of an Ig heavy or TCRβ subunit is called V-D-J joining; the analogous process that generates a rearranged variable region of an Ig light or TCRα subunit is called V-J joining. Sakano, H., et al., *Nature* 280: 288–294 (1979); Early, P., et al., *Cell* 19: 981–992 (1980); Alt, F. W., et al., *Science* 238: 1079–1087 (1987); Harlow, E., and Lane, D., *Antibodies: A Laboratory Manual*, Cold Spring Harbor Laboratory (1988), pages 10–18; Davis, M. M., and Bjorkman, P. J., *Nature* 334: 395–404 (1988). Additionally, point mutations are introduced throughout the variable region by a process called somatic mutation. Bernard, O., et al., *Cell* 15: 1133–1144 (1978).

A functionally rearranged Ig or TCR subunit gene is one in which the DNA rearrangements of V-D-J or V-J joining and/or somatic mutation have not resulted in a reading frame that is prematurely terminated during biosynthesis because of the introduction of stop codons or frameshifting mutations. Because each T or B cell of the immune system expresses genes encoding their respective antigen receptors in which a unique functionally rearranged variable region is present, many different T or B cells, each producing a receptor that has a unique antigen-recognizing region, are generated. The total catalog of different antigen receptors displayed on the T cells of an animal is referred to as the animal's TCR repertoire. Bevan, M. J., *Science* 264: 796–797 (1994).

For mature T or B cells, binding of antigen to a cell's antigen receptor activates the cell, i.e., stimulates the cell to undertake activities related to generating a cell-mediated or humoral immune response. In contrast, for immature T or B cells, binding of antigen to a displayed TCR or B cell antigen receptor, respectively, results in elimination of the cell by a process called negative selection or clonal deletion. Clonal deletion occurs during normal development of a healthy wildtype animal, and is a mechanism by which the immune system learns to tolerate the animal's normal endogenous (self) antigens, i.e., to treat the animal's self antigens as non-immunogenic antigens. Failure of the immune system to achieve or maintain tolerance of self antigens may result in autoimmune responses (i.e., autoimmune response to self antigens) that can culminate in autoimmune disease in animals including humans. Autoimmune disease can occur when an appropriate immune response to a non-self antigen results in the production of immune effector biomolecules (e.g., autoantibodies) or cells that cross-react with self antigens. Human autoimmune diseases include such crippling conditions as Multiple Sclerosis (MS) and Systemic Lupus Erythematosus (SLE). For a review, see Steinman, L., *Sci. American* 269: 107–114 (1993).

Although B cells can directly bind soluble antigen, T cells respond to antigen only when it is displayed on specific classes of other cells known generically as an antigen-presenting cells (APCs). APCs, e.g., macrophages and dendritic cells, present antigens derived from polypeptides via glycoproteins, known as MHC (major histocompatibility complex) proteins, which are displayed on the surface of APCs. Bevan, M. J., et al., *Science* 264: 796–797 (1994). MHC proteins bind antigens generically; the specificity determinants in a TCR:Ag:MHC complex are (1) the unique polypeptide sequences of the variable portion of the TCR and (2) the unique polypeptide sequences of antigen. However, to some degree, MHC-presented oligopeptide antigens are embedded within an MHC molecule and TCR recognition of antigen only occurs within the context of an appropriate class of MHC molecule. Janeway, C. A., *Sci. American* 269: 73–79 (1993). This phenomenon, called MHC restriction, is of fundamental importance to T cell antigen recognition and physiology. Zinkernagel, R. M., and Doherty, P. C., *Nature* 248: 701–702 (1974).

The genes encoding MHC proteins are diverse; however, unlike Ig and TCR molecules, which vary from cell to cell in an individual animal, MHC antigens vary from individual animal to individual animal or from one group of related individual animals to another group. Members of familial groups, represented in the mouse by inbred strains of mice, share similar MHC antigens with each other, but not with individuals from other strains of mice. Snell, G. D., *Science* 213: 172–178 (1981). Because variant MHC molecules will be capable of binding different antigens, the antigens that T cells will be able to recognize (i.e., bind in the MHC context) and respond to varies among different strains of mice. In humans, particular MHC variant molecules are more highly associated with autoimmune diseases, presumably because these MHC variant molecules are more competent at binding (and thus presenting to T cells) self antigens. Vaughan, in *Immunological Diseases*, 3rd Ed., Vol. II, Samter, M., ed., pp. 1029–1037 (1978); Steinman, L., *Sci. American* 269: 107–114 (1993).

Arthritis is a painful manifestation of many human autoimmune diseases. The etiology of arthritis is, in most cases, unknown. Inflammatory lesions of synovial joints occur in general autoimmune diseases such as SLE, but are more frequently present in specific autoimmune diseases such as Rheumatoid Arthritis (RA) or Reactive Arthritis (ReA). RA, the prototypic arthritic disease, occurs in an otherwise globally normal immunological context. RA is a chronic inflammatory disease that is characterized by the development of one or more synovial membranes into a highly vascularized tissue known as the pannus. The pannus consists of several distinct types of cells, including resident synovial fibroblasts as well as infiltrating mononuclear cells that can produce inflammatory effector and mediator biomolecules. The pannus exhibits invasive growth into surrounding tissues with a corresponding progressive destruction of articular cartilage and bone. Harris, E. D., Jr., in *Textbook of Rheumatology*, Kelly, W., et al., Eds., W. B. Saunders Co., Philadelphia, pages 905–942 (1989).

Symptoms of rheumatoid arthritis range from swelling of one or more joints and associated pain to comparatively mild morning stiffness affecting one or more joints of the limbs. In severe cases, chronic inflammation results in destruction and deformity of the cartilage and bone in the joints, accompanied by chronic pain and physical deformation of the affected limbs. Chronic pain and deformation have obviously serious consequences in regard to the loss of joint mobility and quality of life of affected individuals. Generally, 50% of patients with RA can lead fairly normal lives; about 25% are partially incapacitated, with gradually progressing disability; and about 25% lead greatly restricted lives. A small proportion (less than 10%) of RA patients are totally disabled. Christian, C. L., and Paget, S. A., "Rheumatoid Arthritis" in *Immunological Diseases*, Vol. II, 3rd Ed., Samter, M., Ed., Little, Brown and Co., pages 1061–1076 (1978).

RA is a frequent human disease, affecting close to 1% of the human populations of developed countries, which has a complex component of genetic predisposition. Wordsworth, P., *Current Opinion in Immunology* 4: 766–769 (1992). RA is also observed in domestic animals, especially dogs. Tizard, pp. 527–528. Some studies indicate that, in humans, RA is two to three times more common in females than in males. Christian, C. L., and Paget, S. A., "Rheumatoid Arthritis" in *Immunological Diseases*, Vol. II, 3rd Ed., Samter, M., Ed., Little, Brown and Co., pages 1061–1076 (1978). It has been suggested that the female hormone estrogen stimulates DNA sequences that indirectly induce the production of γ-interferon, which stimulates the appearance of human MHC molecules in synovial joint linings, where they are not normally found. Fox, H. S., et al., *J. Immunol.* 146: 4362–4367 (1991).

The cause of rheumatoid arthritis is currently unknown and, in the absence of clear evidence, the subject of debate. The disease develops as follows. Histologically, the affected joints are infiltrated by cells of the hemopoietic lineage (lymphocytes, macrophages, and/or neutrophils) which produce inflammatory cytokines. The synovial lining itself is hyperplasmic and forms, together with inflammatory cells, a granuloma-like "pannus" which erodes and invades the cartilage and bone. Enzymes derived from the exudative and proliferative processes of inflammation hydrolyze various substrates in cartilage, bone, ligaments and tendons, resulting in structural deformation of synovial joints. As RA progresses, the infiltrating neutrophils may be supplemented or partially replaced by $CD4^+$ lymphocytes, which can form lymphoid nodules and germinal centers. Rheumatoid factors, autoantibodies of the IgM class directed to antibodies of the IgG class, are present in the sera of some but not all patients. Christian, C. L., and Paget, S. A., "Rheumatoid Arthritis" in *Immunological Diseases*, Vol. II, 3rd Ed., Samter, M., Ed., Little, Brown and Co., pages 1061–1076 (1978).

Although the terminal events of the pathogenesis of RA are relatively well understood or at least described, the cellular and molecular causes of initiating and early events of RA have not been described in detail. For example, both cytotoxic and humoral immune responses have been described in previously known RA models. Chioechia, G., et al., *J. Immunol.* 145: 519–525 (1990). Indeed, whether RA represents an immune response to self antigens with secondary inflammatory consequences, or a primary dysregulation of macrophage function, has been a matter of debate. Firestein, G. S., and Zwaifler, N. J., *Arthritis and Rheumatism* 33: 768–773 (1990); Lanchbury, J. S., and Pitzalis, C., Current Opinion in Immunology 5: 918–924 (1993). Although some candidate self antigens have been proposed for RA, none has been conclusively identified. Sano, H., et al., *J. Cell Biol.* 110: 1417–1426 (1990).

Current animal models of RA include the following immunologic models. For a review, see Schwartz, R. S., in *Fundamental Immunology*, 3rd Ed., Paul, W. E., ed., Raven Press, N.Y., pages 1064–1067 (1993).

1. Collagen induced arthritis (CIA) seems mainly dependent on autoantibodies. It is induced by immunization of rats or mice with type II collagen (the type that is prevalent in joint cartilage), or by administration of antibodies to type II collagen. Collagen-specific T helper cells can also transfer the disease. IgG antibodies are concentrated in the synovial fluids and form deposits in the joint, presumably leading to inflammation. A similar rabbit model exists but is less well-characterized. Jasin, H. E., *Fed. Proc. (USA)* 32: 147–152 (1973).

2. Adjuvant arthritis is induced in susceptible strains of rats by injection of *Mycobacterium tuberculosis* in oil. Joint inflammation and swelling of the joints ensues, predominantly in the distal parts of the limbs, which is transitory and disappears after 21 days, leaving sequellar destruction. Pearson, C. M., *J. Chronic Dis.* 16: 863–874 (1963). In this case, the disease is transferable from rats with disease to naive animals with T lymphocyte populations or lines. It appears that the T cells and/or antibodies elicited by immunization with *M. tuberculosis* may be cross-reactive between proteoglycan structures in the bacteria and cartilage. Pristane-induced arthritis (PIA) is similarly induced by injection of the drug pristane in mineral oil. Potter, M., and Wax, J. S., *J. Immunol.* 127: 1591–1595 (1981).

3. Lpr/fas arthritis occurs in mice of the MRL/lpr strain which carry a mutation in the fas gene, involved in the induction of cell death through apoptosis. As a result of this deficiency, a massive lymphoproliferation occurs in these mice, primarily composed of an unusual population of T lymphocytes. Several autoimmune manifestations result, including progressive inflammation of joints. Cheng, J., et al., *Science* 263: 1759–1762 (1994).

None of these models is quite satisfying. In CIA, adjuvant arthritis and PIA, the animal is artificially immunized with antigens that result in an immune response that cross-reacts with cartilage-borne biomolecules; for example, all three form of arthritis can be treated by teaching the immune system tolerance for type II collagen. Thompson, H. S. G., and Staines, N. A., *Clin. Exp. Immunol.* 64: 581–586 (1985); Zhang, Z. J., et al., *J. Immunol.* 145: 2489–2493 (1990); Thompson, S. J., et al., *Immunol.* 79: 152–157 (1993). However, destruction of cartilage-associated structures occurs late in RA, possibly as a secondary effect, so these models likely do not reflect arthritis in which primary or early events in the immune system result in a cascade of autoimmunological events that culminates in arthritis. Lpr/fas arthritis is a lymphoproliferative disease with only secondary arthritic consequences, a setting that is clearly different from the globally normal immunological context of RA. An animal model that incorporates the method of CIA into an autoimmune disease prone background results in more severe arthritic symptoms but suffers from both of the above drawbacks. Watson, W. C., et al., *J. Exp. Med.* 172: 1331–1339 (1990).

Moreover, none of the above immunologic methods provides an animal model in which the animal develops severe arthritic symptoms in a reproducible and thus predictable manner, thus allowing the characterization and manipulation of early immunologic events in PA. Recently, the ability to produce transgenic animals has provided an opportunity to develop animal models that more faithfully reflect human diseases, including autoimmune diseases. Watson, J. D., et al., "The Introduction of Foreign Genes Into Mice," in *Recombinant DNA*, 2d Ed., W. H. Freeman & Co., New York (1992), pp. 255–272; Lee, M.-S., and Sarvetnick, N., *Curr. Op. Immunol.* 4: 723–727 (1992). A transgenic animal is an animal into which has been introduced by unnatural means (i.e., by human manipulation), one or more genes that do not occur naturally in the animal, e.g., foreign genes, genetically engineered endogenous genes, etc. The unnaturally introduced genes, known as transgenes, may comprise foreign DNA sequences, i.e., sequences not normally found in the genome of the host animal. Alternatively or additionally, transgenes may comprise endogenous DNA sequences that are abnormal in that they have been rearranged or mutated in vitro in order to alter the normal in vivo pattern of expression of the gene, or to alter or eliminate the biological activity of an endogenous gene product encoded by the gene. Watson, J. D., et al., "The Introduction of Foreign Genes Into Mice," in *Recombinant DNA*, 2d Ed., W. H. Freeman & Co., New York (1992), pp. 255–272; Gordon, J. W., *Intl. Rev. Cytol.* 115: 171–229 (1989); Jaenisch, R., *Science* 240: 1468–1474 (1989); Rossant, J., *Neuron* 2: 323–334 (1990).

In the course of investigating the immune system, scientists have generated several transgenic TCR animals, i.e., animals which comprise a transgene that directs the expression of a particular TCR or TCR subunit. Krimpenfort, P., et al., *EMBO Journal* 7: 45–50 (1988); Teh, H. S., et al., *Nature* 335: 229–233 (1988); Bluthmann, H., et al., *Nature* 334: 156–159 (1988); Uematsu, Y., et al., *Cell* 52: 831–841 (1988); Steinmetz, M., et al., *Genome* 31: 652–655 (1989); Berg, L. J., et al., *Cell* 58: 1035–1046 (1989); Uematsu, Y., *Eur. J. Immunol.* 22: 603–606 (1992); Borgulya, P., et al., *Cell* 69: 529–537 (1992); Katz, J. D., et al., *Cell* 74: 1089–1100 (1993). Introduction of a transgenic TCR "knockout" (loss of function) allele into mice results in animals which are substantially depleted for T cells. Krimpenfort, P. J. A., and Berns, A. J. M., U.S. Pat. No. 5,175,384 (Dec. 29, 1992). More subtle biological effects result from the introduction of transgenic TCR alleles which confer altered specificities to an animal's T cells. However, the introduction of a transgenic TCR allele derived from a T cell clone capable of transferring collagen-induced arthritis into mice does not result in arthritis in the resultant transgenic animals. Mori, L., et al., *J. Exp. Med.* 176: 381–388 (1992).

The references discussed above and elsewhere herein are provided solely for the disclosure prior to the filing date of the present application and nothing herein is to be construed as an admission that the inventors are not entitled to antedate such disclosures by virtue of prior invention.

Given the state of the art, a need exists for animal models in which the animal develops severe arthritic symptoms in a reproducible and thus predictable manner, in order to characterize and control early immunologic events in autoimmune arthritis, particularly rheumatoid arthritis. Accordingly, it is an object herein to provide transgenic non-human animals that have been genetically engineered to develop autoimmunological arthritis by virtue of the fact that the T cell receptor (TCR) populations of the transgenic animals consist substantially of copies of a TCR that (a) comprises transgene encoded TCRα and TCPβ subunits and (b) directs T cells to react with self antigens during development of the transgenic animals to initiate a cascade of autoimmunological events that culminates in the transgenic animals developing severe arthritic symptoms in a reproducible and thus predictable manner.

It is also an object herein to provide materials and methods for making transgenic non-human arthritic animals, some of which can be used to generate therapeutic anti-arthritic compositions.

It is a further object herein to provide methods of using the transgenic non-human arthritic animals to evaluate the anti-arthritic or arthitogenic potential of various compositions of matter, including animal and human genes and the gene products encoded thereby.

Further, it is an object herein to provide hybridomas derived from B or T cells of the transgenic non-human arthritic animals, and specific biomolecules produced in association with transgene associated arthritis by the hybridomas and the B and T cells from which they are derived.

Still further, it is an object herein to provide an isolated protein endogenous to animals including humans which comprises polypeptide arthitogenic self antigens, methods of purifying or producing the isolated protein, and methods of using the isolated protein or compositions derived therefrom to treat human and animal arthritic diseases.

SUMMARY OF THE INVENTION

The invention is based on the unexpected discovery that transgenic non-human animals having a limited TCR repertoire that consists substantially of transgene encoded TCRs have a phenotype that selectively comprises severe classical symptoms of rheumatoid arthritis. The TCR repertoire of the arthritic animal, albeit limited, is functionally viable. The limited TCR repertoire of the arthritic animal consists in substantial part of a class of TCRs that recognize an epitope of an endogenous polypeptidic arthritogenic antigen. In a preferred embodiment, the invention relates to transgenic arthritic mice wherein an arthritic phenotype is present due to the insertion into the genomes of the mice of transgenes encoding TCR α and β subunits that combine in T cells of a transgenic animal to form a TCR that recognizes an antigen comprising one or more epitopes of an oligopeptide corresponding to amino acids 41–61 of bovine pancreatic ribonuclease (BPR) and having the amino acid sequence Lys–Pro–Val–Asn–Thr–Phe–Val–His–Glu–Ser–Leu–Ala–

Asp–Val–Gln–Ala–Val–Cys–Ser–Gln–Lys [SEQ ID NO. 1], and/or one or more epitopes of an endogenous polypeptide arthritogenic self antigen that are substantially cross-reactive with those of the BPR-derived oligopeptide.

In one aspect, the invention provides an animal model for arthritis. Because of the crippling and painful nature of arthritis in affected individuals, as well as its economic consequences to society, it is desired to obtain the benefit of a reliable and reproducible animal model of arthritis. The transgenic animal model of the invention provides a model in which the animals develop severe arthritic symptoms in a reliable and reproducible manner. The reliability and reproducibility of the transgenic animal model of the invention are not found in previously known animal models of arthritis.

In a related aspect, the invention provides (1) methods for producing a transgenic non-human animal which has a limited TCR repertoire due to the expression therein of transgenes encoding TCR α and β subunits and (2) means for generating the transgenic animals of the invention, including isolated DNA molecules capable of expressing DNA sequences encoding the variable and constant regions of the α and β subunits in T cells of a transgenic animal in order to direct the formation of a TCR that recognizes an antigen comprising one or more epitopes of an oligopeptide corresponding to amino acids 41–61 of bovine pancreatic ribonuclease and having the amino acid sequence Lys–Pro–Val–Asn–Thr–Phe–Val–His–Glu–Ser–Leu–Ala–

Asp–Val–Gln–Ala–Val–Cys–Ser–Gln–Lys [SEQ ID NO. 1], and/or one or more epitopes of an endogenous polypeptide arthritogenic self antigen. Oligopeptides derived from the amino acid sequence of the TCR variable regions of the invention are used to design therapeutic compositions.

In another aspect, the invention provides methods of using the animal model of the invention to (1) test compositions for their anti-arthritic (therapeutic) potential, and (2) evaluate compositions for their arthritogenic (hazardous) potential.

The transgenic animal of the present invention is also useful as a source of immune system cells and biomolecules that recognize endogenous polypeptide arthritogenic self antigens (PASAs). Hybridomas derived from lymphocytes from transgenic arthritic mice of the invention produce immunologic effector biomolecules that specifically recognize endogenous proteins comprising PASAs. These immune system cells and biomolecules are used to assay the concentration and distribution of PASA-comprising proteins in animals including humans.

Utilizing the one or more of the mice or cell lines of the present invention, or immunologic effector biomolecules produced thereby, the present invention further provides methods of identifying and purifying endogenous proteins comprising PASAs from animals including humans. Thus, in another aspect, the invention provides isolated endogenous proteins comprising PASAs, and, in a related aspect, the invention provides for oligopeptides derived from the isolated endogenous proteins comprising PASAs. Means and methods of producing the isolated endogenous proteins comprising PASAs from biological fluids from animals including humans, as well as by expression through recombinant DNA technology, are also provided.

In yet another aspect, the invention provides therapeutic compositions for rheumatoid arthritis comprising isolated endogenous proteins comprising PASAs, one or more isolated oligopeptides comprising amino acid sequences derived from the polypeptide sequence of the endogenous proteins comprising PASAs, or one or more synthetic polypeptides derived from the amino acid sequences of the variable regions of the TCR subunits expressed by hybridoma R28.

BRIEF DESCRIPTION OF THE DRAWINGS

In FIGS. 3(A–B), cells from the lymph node of the mice were stained with polyclonal antibodies directed to an epitope composed of aligned portions of the TCRα and TCRβ subunits of hybridoma R28. In FIGS. 3(C–D), cells were stained with a monoclonal antibody specific for the Vβ6 portion of the variable region used in the gene for the TCRβ subunit of hybridoma R28 and other functionally rearranged TCRβ genes.

DETAILED DESCRIPTION OF THE DISCLOSURE

Terms and Symbols

Figure 1A:
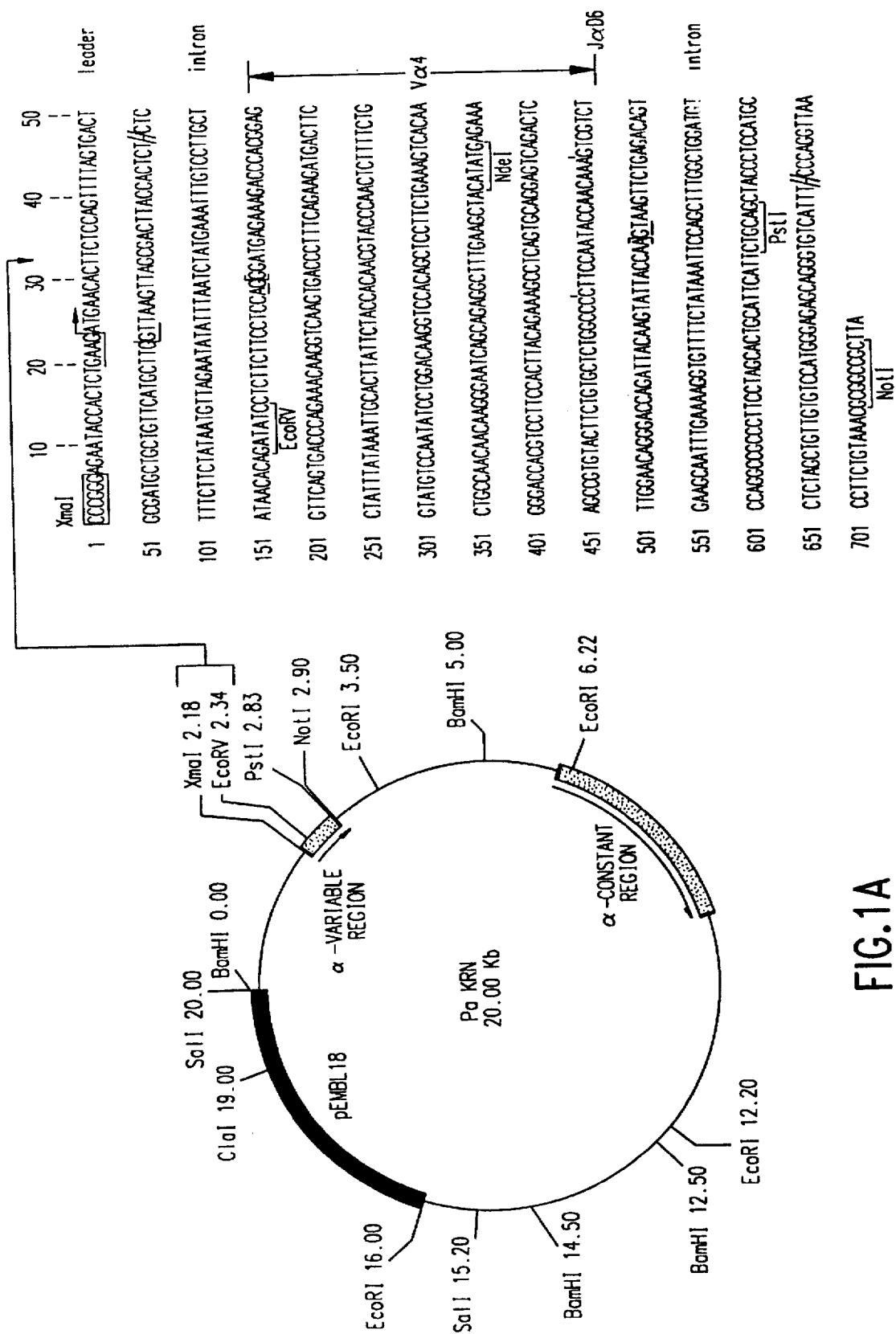
FIGS. 1(A–B) depicts the plasmids used to construct KRN transgenic mice. Panel A of FIG. 1 depicts paKRN, which is composed of DNA sequences from a prokaryotic vector, pEMBL18 (thick line) and approximately 16 kb of DNA sequences from the functionally rearranged TCRα allele from hybridoma R28. The exons (coding sequences) of the TCRα subunit are stippled, and the direction of their transcription is indicated by arrows; non-coding sequences (introns and sequences flanking the exons) are shown by thin lines. The DNA sequence of the exon encoding the variable region of the TCRα subunit is given in the inset [SEQ ID NO. 2]; note that a short intron which interrupts the coding sequence of the variable region but which is excised in mature mRNA is not shown on the plasmid diagram for the sake of clarity. Panel B of FIG. 1 depicts pbKRN, which is composed of DNA sequences from a prokaryotic vector, pTZ18 (thick line) and approximately 18 kb of DNA sequences from the functionally rearranged TCRβ allele from hybridoma R28. Other symbols are as in Panel A of FIG. 1, except that the exons encoding the TCRβ subunit are hatched. The DNA sequence of the exon encoding the variable region of the TCRβ subunit is given in the inset [SEQ ID NO. 3].

For purposes of this disclosure, the following abbreviations, definitions, genetic designations and restriction enzyme recognition sequences are used herein unless otherwise indicated.

TABLE 1

| ABBREVIATIONS | |
|---|---|
| Ag = | antigen |
| APC = | antigen presenting cell |
| BPR = | bovine pancreatic ribonuclease |
| CD = | cluster of differentiation |
| cDNA = | complementary deoxyribonuclease acid |
| D = | diversity (gene segment) |
| DNA = | deoxyribonucleic acid |
| EAE = | experimental allergic encephalomyelitis |
| ES = | embryonic stem |

TABLE 1-continued

ABBREVIATIONS

| | |
|---|---|
| FCS = | fetal calf serum |
| HLA = | human lymphocyte antigen |
| HPLC = | high pressure liquid chromatography |
| Ig = | immunoglobulin |
| J = | joining (gene segment) |
| MHC = | major histocompatibility complex |
| mRNA = | messenger ribonucleic acid |
| MS = | multiple sclerosis |
| NOD = | nonobese diabetic (strain of mice) |
| PASA = | polypeptide arthritogenic self antigen |
| PCR = | polymerase chain reaction |
| RA = | rheumatoid arthritis |
| RNA = | ribonucleic acid |
| RNase = | ribonuclease |
| ReA = | reactive arthritis |
| REN = | restriction endonuclease |
| TCR = | T cell receptor |
| Tg = | transgenic |
| tRNA = | transfer ribonucleic acid |
| V = | variable (gene segment) |

Glossary

Affinity chromatography: Chromatography in which the relatively immobilized substance has an affinity for a specific component of the mixture which is being chromatographed.

Amino acid sequence: The sequence of a polypeptide given in the order of from amino terminal (N-terminal), to carboxy terminal (C-terminal). Synonymous with "polypeptide sequence," "peptide sequence," "protein sequence," or "primary protein sequence."

Animal: (1) Excludes human beings, individually and collectively, in all stages of development, including embryonic and fetal stages, unless otherwise indicated; and (2) includes all other vertebrate animals, including an individual animal in any stage of development, including embryonic and fetal stages. "Non-human animal" has the same meaning as "animal."

Animal model: A non-human animal that faithfully mimics a human disease and in which potential therapeutic compositions or potentially hazardous compositions may be evaluated for their effect on the disease.

Antibody: A protein molecule synthesized by a B-cell upon exposure to antigen capable of combining specifically with that antigen. Synonymous with immunoglobulin (Ig).

Antigen: A molecule or composition of matter which (1) induces an immune response in an animal, and (2) interacts specifically with antigen-recognizing components of an immune animal's immune system.

Self antigen: A normal endogenous molecule or composition of matter in an animal which is an antigen in an autoimmune disease. Synonymous with autoantigen.

Biomolecule: A molecule produced by a living organism. Synonymous with "biological molecule."

Biochemical synthesis: The synthetic production of a biomolecule wherein other biomolecules are utilized in the production.

Biosynthesis: The production of a biomolecule by a living organism.

Carrier: A molecule required in combination with a hapten in order for an immune response to the hapten to occur. That is, a molecule which puts a hapten in a molecular context in which the hapten has enhanced immunogenicity.

Chemical synthesis: The synthetic production of a biomolecule in the absence of any other biomolecules and without requiring the use of any other biomolecules.

Chromatography: A process characterized by the uniform and uninterrupted flow of a mixture (gas or liquid) through a region of a stationary phase (liquid or solid) which, through various means, allows for the differential migration of the components of the mixture.

Detectable label: A chemical moiety that is coupled to a biomolecule to enable detection of the biomolecule and which may be selected from the group consisting of a radiolabel, an enzyme such as horseradish peroxidase or alkaline phosphatase, streptavidin, biotin, an epitope recognized by an antibody, and equivalents thereof.

Detectably labelled: A state of a biomolecule in which the biomolecule has covalently attached to it a detectable label.

Disease: (1) Excludes pregnancy per se but not autoimmune diseases associated with pregnancy, and (2) includes any abnormal condition of an organism or part, especially as a consequence of infection, inherent weakness, environmental stress, that impair normal physiological functioning.

DNA sequence: The sequence of contiguous nucleotide bases of a strand of DNA as read from 5' to 3'. Synonymous with "DNA molecule."

Enzyme: Protein that is a catalyst for a specific chemical reaction, often one involving one or more biomolecules as substrates and/or products. Unlike non-biologically derived catalysts, enzymes may recognize a substrate with stereospecificity, i.e., some enzymes are capable of recognizing, and thus catalyzing the chemical reaction of, only one of a pair of L- and D-enantiomers.

Epitope: A part of an antigen that interacts specifically with antigen-recognizing components of an animal's immune system. In a polypeptidic antigen, epitopes may correspond to short sequences of contiguous amino acids; the remainder of the antigen is called the carrier. Synonymous with antigenic determinant.

Expression vector: An artificial DNA sequence or a naturally-occurring DNA sequence that has been artificially modified, into which foreign or abnormal genes can be inserted for expression thereof in host organisms appropriate for the vector.

Foreign or abnormal: Non-endogenous to a healthy, wild-type animal. "Foreign or endogenous but abnormal antigens" designates biomolecules that an immune response should be generated towards and includes both biomolecules from invasive pathogens and animal-encoded biomolecules present on cancerous or infected cells; synonymous with "non-self." "Foreign or abnormal genes" designates DNA sequences that are not endogenous to an animal's genome, or animal-derived DNA sequences that have been rearranged, mutated, or otherwise genetically-engineered so as to possess properties (e.g., genomic location, regulation of expression, copy number) not possessed by the endogenous DNA sequences from which they were derived.

Gene: A DNA sequence that consists of a structural gene, e.g., a reading frame that encodes a polypeptide sequence, according to the standard genetic code (Table 2); and expression elements, e.g., promoters, terminators, enhancers, etc., required for transcription of the structural gene.

Genetically engineered: Subject to human manipulation intended to introduce genetic change.

Hapten: A small molecule which (1) cannot, by itself, induce an immune response in an animal, (2) can, in combination to a carrier to which it is bound, induce an immune response in an animal, and (3) interacts specifically with the antigen-recognizing components of an immune animal's immune system.

Host animal: An animal that harbors foreign and/or abnormal genes introduced as a result of (1) invasion of cells of the animal by a naturally occurring or genetically engineered intracellular parasite; or (2) introduction into cells of foreign or abnormal genes by human manipulation.

Immune animal: An animal which has been presented with an immunizing amount of antigen and has generated a humoral and/or cell-mediated immune response thereto.

Isoschizomer: One of a set of restriction enzymes that are functionally equivalent by virtue of each having the same recognition sequence.

Mammal: (1) Excludes human beings, individually and collectively, in all stages of development, including embryonic and fetal stages, unless otherwise indicated; and (2) includes all other animals that are members of the vertebrae class Mammalia, including an individual animal in any stage of development, including embryonic and fetal stages, distinguished by self-regulating body temperature, hair, and, in the females, milk-producing mammae.

Monoclonal antibody: A unique, isolated antibody molecule produced by a hybridoma.

Monospecific antibody: A polyclonal antibody produced in immunological response to a single or few epitopes found in (1) a short, isolated, synthetic antigen or (2) a short, isolated, carrier-bound hapten.

Polyclonal antibody: A composition that comprises an assortment of different antibodies that all recognize a particular antigen.

Polypeptide: A polymer of amino acid residues.

Protein: A biomolecule comprising one or more polypeptides arranged into a functional, three-dimensional form.

Recombinant biosynthesis: Synthesis in an organism that is directed towards a particular biomolecule by the natural introduction of genetic material encoding the biomolecule.

Restriction endonuclease: An endonuclease that cleaves DNA at each occurrence therein of a specific recognition sequence. Synonymous with "restriction enzyme."

Transgene: A gene that does not occur naturally in an animal, i.e., a foreign or abnormal gene, introduced into an animal by unnatural means, i.e., by human manipulation.

Transgenic animal: An animal into which has been introduced, by unnatural means, i.e., by human manipulation, one or more transgenes.

TABLE 2

| THE GENETIC CODE | | | | | |
|---|---|---|---|---|---|
| First position | Second position | | | | Third position |
| (5' end) | U | C | A | G | (3' end) |
| U | Phe | Ser | Tyr | Cys | U |
|  | Phe | Ser | Tyr | Cys | C |
|  | Leu | Ser | Stop | Stop | A |
|  | Leu | Ser | Stop | Trp | G |
| C | Leu | Pro | His | Arg | U |
|  | Leu | Pro | His | Arg | C |
|  | Leu | Pro | Gln | Arg | A |
|  | Leu | Pro | Gln | Arg | G |
| A | Ile | Thr | Asn | Ser | U |
|  | Ile | Thr | Asn | Ser | C |
|  | Ile | Thr | Lys | Arg | A |
|  | Met | Thr | Lys | Arg | G |
| G | Val | Ala | Asp | Gly | U |
|  | Val | Ala | Asp | Gly | C |
|  | Val | Ala | Glu | Gly | A |
|  | Val | Ala | Glu | Gly | G |

Throughout the disclosure, abbreviations for amino acid and nucleotide residues present in, respectively, polypeptide and nucleic acid sequences, are as described in 37 C.F.R. § 1,822, revised as of Jul. 1, 1993.

TABLE 3

| REN RECOGNITION SEQUENCES | |
|---|---|
| REN | Recognition Sequence |
| BamHI | GGATCC |
| EcoRI | GAATTC |
| EcoRV | GATATC |
| KpnI | GGTACC |
| NdeI | CATATG |
| NruI | TCGCGA |
| NotI | GCGGCCGC |
| PstI | CTGCAG |
| SacII | CCGCGG |
| SalI | GTCGAC |
| XhoI | CTCGAG |
| XmaI | CCCGGG |

DETAILED DESCRIPTION OF THE DISCLOSURE

The invention is based on the unexpected discovery that non-human animals having a substantially limited repertoire of T cell receptors display a phenotype selectively comprising severe classical symptoms of rheumatoid arthritis. The TCR repertoire of the arthritic animals, albeit limited, is functionally viable. The limited TCR repertoire of the arthritic animals consists in substantial part of TCRs that recognize one or more epitopes of endogenous polypeptide arthritogenic self antigens. In a preferred embodiment, the limited TCR repertoires of the arthritic animals result from the insertion into the genome of the animals of transgenes encoding TCR α and β subunits that combine in T cells of the resultant transgenic animals to form a TCR that binds an antigen comprising one or more epitopes of an oligopeptide corresponding to amino acids 41–61 of bovine pancreatic ribonuclease (BPR) and having the amino acid sequence Lys-Pro-Val-Asn-Thr-Phe-Val-His-Glu-Ser-Leu-Ala- Asp-Val-Gln-Ala-Val-Cys-Ser-Gln-Lys [SEQ ID NO. 1], and/or one or more epitopes of a protein comprising endogenous polypeptide arthritogenic self antigens that are substantially cross-reactive with those of the BPR-derived oligopeptide.

The non-human animals of the invention comprise any animal having an arthritic phenotype as a result of transgenic expression of antigen-recognizing subunits of a T cell receptor that recognizes and/or binds one or more epitopes of amino acids 41–61 of bovine pancreatic ribonuclease and/or endogenous polypeptide arthritogenic self antigens (PASAs). Such non-human animals include vertebrates such as rodents, non-human primates, sheep, dog, cow, amphibians, reptiles, etc. Preferred non-human animals are selected from non-human mammalian species of animals, most preferably, animals from the rodent family including rats and mice, most preferably mice.

The transgenic animals of the invention are animals into which has been introduced by unnatural means (i.e., by human manipulation), one or more genes that do not occur naturally in the animal, e.g., foreign genes, genetically engineered endogenous genes, etc. The unnaturally introduced genes, known as transgenes, may be from the same or a different species as the animal but not naturally found in the animal in the configuration and/or at the chromosomal locus conferred by the transgene. Transgenes may comprise foreign DNA sequences, i.e., sequences not normally found in the genome of the host animal. Alternatively or additionally, transgenes may comprise endogenous DNA sequences that are abnormal in that they have been rearranged or mutated in vitro in order to alter the normal in vivo pattern of expression of the gene, or to alter or eliminate the biological activity of an endogenous gene product encoded by the gene. Watson, J. D., et al., "The Introduction of Foreign Genes Into Mice," in *Recombinant DNA*, 2d Ed., W. H. Freeman & Co., New York (1992), pp. 255–272; Gordon, J. W., *Intl. Rev. Cytol.* 115: 171–229 (1989); Jaenisch, R., *Science* 240: 1468–1474 (1989); Rossant, J., *Neuron* 2: 323–334 (1990).

The transgenic non-human animals of the invention are produced by introducing transgenes into the germline of the non-human animal. Embryonal target cells at various developmental stages are used to introduce the transgenes of the invention. Different methods are used depending on the stage of development of the embryonal target cell(s).

1. Microinjection of zygotes is the preferred method for incorporating transgenes into animal genomes in the course of practicing the invention. A zygote, a fertilized ovum that has not undergone pronuclei fusion or subsequent cell division, is the preferred target cell for microinjection of transgenic DNA sequences. The murine male pronucleus reaches a size of approximately 20 micrometers in diameter, a feature which allows for the reproducible injection of 1–2 picoliters of a solution containing transgenic DNA sequences. The use of a zygote for introduction of transgenes has the advantage that, in most cases, the injected transgenic DNA sequences will be incorporated into the host animal's genome before the first cell division. Brinster, et al., *Proc. Natl. Acad. Sci. (USA)* 82: 4438–4442 (1985). As a consequence, all cells of the resultant transgenic animals (founder animals) stably carry an incorporated transgene at a particular genetic locus, referred to as a transgenic allele. The transgenic allele demonstrates Mendelian inheritance: half of the offspring resulting from the cross of a transgenic animal with a non-transgenic animal will inherit the transgenic allele, in accordance with Mendel's rules of random assortment.

2. Viral integration can also be used to introduce the transgenes of the invention into an animal. The developing embryos are cultured in vitro to the developmental stage known as a blastocyte. At this time, the blastomeres may be infected with appropriate retroviruses. Jaenich, R., *Proc. Natl. Sci. (USA)* 73: 1260–1264. Infection of the blastomeres is enhanced by enzymatic removal of the zona pellueida. Hogan, et al., in *Manipulating the Mouse Embryo*, Cold Spring Harbor Press, Cold Spring Harbor, N.Y. (1986). Transgenes are introduced via viral vectors which are typically replication-defective but which remain competent for integration of viral-associated DNA sequences, including transgenic DNA sequences linked to such viral sequences, into the host animal's genome. Jahner, et al., *Proc. Natl. Acad. Sci. (USA)* 82: 6927–6931 (1985); Van der Putten, et al., *Proc. Natl. Acad. Sci. (USA)* 82: 6148–6152 (1985). Transfection is easily and efficiently obtained by culture of blastomeres on a mono-layer of cells producing the transgene-containing viral vector. Van der Putten, et al., *Proc. Natl. Acad. Sci. (USA)* 82: 6148–6152 (1985); Stewart, et al., *EMBO Journal* 6: 383–388 (1987). Alternatively, infection may be performed at a later stage, such as a blastocoele. Jahner, D., et al., *Nature* 298: 623–628 (1982). In any event, most transgenic founder animals produced by viral integration will be mosaics for the transgenic allele; that is, the transgene is incorporated into only a subset of all the cells that form the transgenic founder animal. Moreover, multiple viral integration events may occur in a single founder animal, generating multiple transgenic alleles which will segregate in future generations of offspring. Introduction of transgenes into germline cells by this method is possible but probably occurs at a low frequency. Jahner, D., et al., *Nature* 298: 623–628 (1982). However, once a transgene has been introduced into germline cells by this method, offspring may be produced in which the transgenic allele is present in all of the animal's cells, i.e., in both somatic and germline cells.

3. Embryonal stem (ES) cells can also serve as target cells for introduction of the transgenes of the invention into animals. ES cells are obtained from pre-implantation embryos that are cultured in vitro. Evans, M. J., et al., *Nature* 292: 154–156 (1981); Bradley, M. O., et al., *Nature* 309: 255–258 (1984); Gossler, et al., *Proc. Natl. Acad. Sci. (USA)* 83: 9065–9069 (1986); Robertson et al., *Nature* 322: 445–448 (1986). ES cells that have been transformed with a transgene can be combined with an animal blastocyst, whereafter the ES cells colonize the embryo and contribute to the germline of the resulting animal, which is a chimera (composed of cells derived from two or more animals). Jaenisch, R., *Science* 240: 1468–1474 (1988). Again, once a transgene has been introduced into germline cells by this method, offspring may be produced in which the transgenic allele is present in all of the animal's cells, i.e., in both somatic and germline cells.

Although the initial introduction of a transgene is a Lamarckian (non-Mendelian) event, the transgenes of the invention may be stably integrated into germ line cells and transmitted to offspring of the transgenic animal as Mendelian loci. Other transgenic techniques result in mosaic transgenic animals, in which some cells carry the transgenes and other cells do not. In mosaic transgenic animals in which germ line cells do not carry the transgenes, transmission of the transgenes to offspring does not occur. Nevertheless, mosaic transgenic animals are capable of demonstrating phenotypes associated with the transgenes.

Transgenes may be introduced into animals in order to provide animal models for human diseases. Transgenes that result in such animal models include, e.g., transgenes that encode mutant gene products associated with an inborn error of metabolism in a human genetic disease and transgenes that encode a human factor required to confer susceptibility to a human pathogen (i.e., a bacterium, virus, or other pathogenic microorganism). Leder, P., et al., U.S. Pat. No. 5,175,383 (Dec. 29, 1992); Kindt, T. J., et al., U.S. Pat. No. 5,183,949 (Feb. 2, 1993); Small, J. A., et al., *Cell* 46: 13–18 (1986); Hooper, M., et al., *Nature* 326: 292–295 (1987); Stacey, A., et al., *Nature* 332: 131–136 (1988); Windle, J. J., et al., *Nature* 343: 665–669 (1990); Katz, J. D., et al., *Cell* 74: 1089–1100 (1993). Transgenic animals that are predisposed to a disease may be used to identify compositions that induce the disease and to evaluate the pathogenic potential of compositions known to induce the disease. Berns, A. J. M., U.S. Pat. No. 5,174,986 (Dec. 29, 1992).

In the appropriate strain background, the transgenes of the invention confer a severe arthritic phenotype to transgenic animals as they develop. Although the transgenic genotype is reproducibly transferred to offspring in a Mendelian fashion, the ability of the transgenic phenotype (i.e., arthritis) to be fully manifested varies in different genetic backgrounds. In practicing the invention, it is desirable to maintain the transgenes of the invention in host animals that belong to a strain in which, due to the strain's particular genetic background, the transgenic genotype does not manifest its harmful arthritic phenotype to a detectable or significant degree. An transgenic animal line in which the transgene is maintained and inherited as a Mendelian locus, but in which the manifestation of a harmful transgenic phenotype is reduced or inhibited, is known as a transgenic maintenance line.

In the course of practicing the invention, animals of the transgenic maintenance line are crossed with animals having a genetic background in which the transgene fully manifests a deleterious arthritic phenotype. Offspring that have inherited the transgenes of the invention, and which will thus develop arthritis, are distinguished from littermates that have not inherited transgenes by analysis of genetic material from the offspring for the presence of biomolecules that comprise unique sequences corresponding to sequences of, or encoded by, the transgenes of the invention. For example, biological fluids that contain polypeptides uniquely encoded by the transgenes of the invention may be immunoassayed for the presence of the polypeptides. A more simple and reliable means of identifying transgenic offspring comprises obtaining a tissue sample from an extremity of an animal, e.g., a tail, and analyzing the sample for the presence of nucleic acid sequences corresponding to the DNA sequence of a unique portion or portions of the transgenes of the invention. The presence of such nucleic acid sequences may be determined by, e.g., hybridization ("Southern") analysis with DNA sequences corresponding to unique portions of the transgene, analysis of the products of PCR reactions using DNA sequences in a sample as substrates and oligonucleotides derived from the transgene's DNA sequence, etc.

An animal's collection of diverse T cell receptors, each having α and β with unique variable regions, is referred to as the TCR repertoire. In an individual animal, including a human, with a wildtype, non-suppressed immune system, the TCR repertoire confers to the immune system the ability to properly identify millions of different antigens. Molecular genetic techniques, such as PCR amplification and sequence determination of DNA molecules encoding the variable regions of functionally rearranged TCR genes, can be used to examine the TCR repertoire of an individual animal. Uematsu, Y., *Immunogenet.* 34: 174–178 (1991). In like fashion, the TCR repertoire in a particular tissue or biological fluid can be examined. Oskenberg, J. R., et al., *Proc. Natl. Acad. Sci. (USA)* 86: 988–992 (1989); Oksenberg, J. R., et al., *Nature* 345: 344–346 (1990) and erratum, *Nature* 353: 94 (1991); Uematsu, Y., et al., *Proc. Natl. Acad. Sci. (USA)* 88: 534–538 (1991); Panzara, M. A., et al., *Biotechniques* 12: 728–735 (1992). Introduction of the transgenes of the invention, which encode functionally rearranged TCR subunits, into an animal results in an animal in which the TCR repertoire consists substantially of the transgene expressed TCR. In transgenic TCR animals, endogenous genes for TCR subunits are not expressed due to the phenomena known as allelic exclusion. Alt, F. W., et al., *Cell* 21: 1–12 (1980); Early, P., and Hood, L., *Cell* 24: 1–3 (1981). The expression of a functionally rearranged TCRβ gene in transgenic mice prevents expression of endogenous TCR43 genes, apparently by inhibiting complete V-D-J joining. Weaver, D., et al., *Cell* 42: 117–127 (1985); Krimpenfort, P., et al., *EMBO Journal* 7: 745–750 (1988); Uematsu, Y., et al., *Cell* 52: 831–841 (1988). Transgenic expression of a functionally rearranged TCRβ chain that lacks a variable region suppresses endogenous TCRβ alleles and thus blocks normal T cell maturation. Krimpenfort, P., et al, *Nature* 341: 742–746 (1988); Krimpenfort, P. J. A., et at., U.S. Pat. No. 5,175,384 (Dec. 29, 1992). However, expression of a functionally rearranged TCRα chain does not always prevent rearrangement and expression of the endogenous TCRα genes. Bluthmann, H., et al., *Nature* 334: 156–159 (1988); Borgulya, P., et al., *Cell* 69: 529 (1992). Thus, transgenic expression in an animal of both a functionally rearranged TCRα gene, and a functionally rearranged TCRβ gene that comprises a variable region, results in a transgenic animal that has a functionally viable, albeit limited, TCR repertoire. Thus, in the transgenic animals of the invention, TCRs composed of the two transgene encoded TCR subunits will predominate over other types of TCRs.

The transgenes of the invention may be obtained by isolating or amplifying DNA sequences from genomic sources, br preparation of cDNA molecules from mRNA templates, by chemical or biochemical synthesis, or combinations thereof. The structural portions of the transgenes of the invention comprise exons, comprising portions of the reading frames for particular TCRα and TCRβ subunits, separated by non-TCR encoding introns. The introns are removed from mature mRNA molecules and amino acid sequences corresponding to the introns do not appear in proteins that result from biosynthesis directed by the mature mRNA sequences. Chambon, P., *Sci. American* 244: 60–71 (1981). The structural portions of the transgenes of the invention encode TCRα and TCRβ subunits that comprise variable regions that compose, in the assembled TCR molecule, a variable region that binds an antigen comprising one or more epitopes of an oligopeptide corresponding to amino acids 41–61 of bovine pancreatic ribonuclease (BPR) and having the amino acid sequence Lys–Pro–Val–Asn–Thr–Phe–Val–His–Glu–Ser–Leu–Ala–

Asp–Val–Gln–Ala–Val–Cys–Ser–Gln–Lys [SEQ ID NO. 1], and/or one or more epitopes of proteins comprising endogenous polypeptide arthritogenic self antigens that are substantially cross-reactive with the epitopes of the BPR-derived oligopeptide.

In order to be expressed, the structural portions of the transgenes of the invention must be coupled to a promoter in a functional arrangement. The promoter need not be a naturally occurring promoter. Different types of promoters, directing different levels of expression, may be used to modulate the extent of arthritis in the transgenic animals of the invention. If a constitutive promoter is desired to be used, a viral promoter such as the SV40 early promoter, is preferred. Other promoters may be semi-constitutive or semi-inducible, i.e., having a basal level of expression that may be increased by administering to the transgenic animals particular inducing compositions. A truly inducible promoter, i.e., one that only functions when particular inducing compositions are present, may be used if stringent control of expression is desired. Additional promoter-associated regulatory elements may be include to enhance, decrease or temporally or histologically limit the expression of the transgenes of the invention. By these means, the biochemical, cellular, immunological and biological characteristics of the arthritis generated in the transgenic arthritic animals of the invention may be manipulated or controlled to produce useful variants thereof.

Immunologic methods by which the invention may also be practiced include immunization of the non-human animal with a polypeptide comprising amino acids 41–61 of bovine pancreatic ribonuclease, or an isolated protein comprising polypeptide arthritogenic self antigens (PASAs), or synthetic polypeptides having amino acid sequences derived from the amino acid sequence of the isolated PASA-comprising protein of the invention. Alternatively, transfer of T cells from the transgenic arthritic animals of the invention into non-transgenic animal may be used to establish an autoimmune response therein. Arthritic animals produced by these immunologic methods, however, display the arthritic condition with a lesser degree of reproducibility and predictability of the course of the disease than the transgenic arthritic animals of the invention.

Other features and advantages of the invention will be apparent from the Examples and from the claims.

EXAMPLES

The following Examples serve only to illustrate the invention, and are not to be construed as in any way limiting the invention.

Example 1

Construction of Transgenes Encoding R28 TCR Subunits

This example describes the production of isolated DNA sequences that encode the α and β subunits of the T cell receptor displayed by R28 cells, and transgene constructs derived therefrom.

DNA Sequences Encoding TCR Subunits from Hybridoma R28

R28, also informally referred to as RNAse 37, is a murine T cell hybridoma derived from a B10.A(4R) mouse injected with an oligopeptide corresponding to amino acids 41–61 of Bovine Pancreatic RNAse (BPR). Peccoud, J., et al., *EMBO Journal* 9: 4215–4223 (1990). In vitro, the TCR displayed on R28 responds to the BPR-derived oligopeptide when it is presented by APCs displaying the MHC A$^k$ molecule. When APCs displaying a mutant MHC A$^k$ molecule are used, R28 cross-reactively recognizes an uncharacterized peptide antigen that is either present in fetal calf serum or the synthesis of which is promoted by fetal calf serum, but which is not BPR or the BPR-derived oligopeptide. Dellabona, P., et al., *Eur. J. Immunol.* 21: 209–213 (1991).

DNAs sequences encoding many different V, D and J segments for Ig subunits are present in multiple unexpressed copies in germline DNA; a different but analogous collection of segments for TCR subunits is also present. For example, in the murine genome, the TCRβ subunit gene locus contains two tandemly arranged nearly identical Cβ regions, each of which is preceded by one D and six J segments; the TCRβ locus also contains 20 to 30 V segments. Davis, M. M., and Bjorkman, P. J., *Nature* 334: 395–402 (1988). During development of an animal, diverse variable regions are generated in individual cells of the immune system by the random joining of different V, D and J (for TCRβ), or V and J (for TCRα) gene segments. At or about the same time, one or more nucleotides is inserted at the junction points of the gene segments, generating additional diversity in the gene segments encoding variable regions, particularly in the case of TCR variable regions. Sakano, H., et al., *Nature* 280: 288–294 (1979); Early, P., et al., *Cell* 19: 981–992 (1980); Davies, M. M., and Bjorkman, P. J., *Nature* 334: 395–402 (1988).

The functionally rearranged variable and joining regions of both the α and β chains of the TCR were cloned and sequenced according to standard procedures. A functionally rearranged TCR or Ig subunit gene is one in which the DNA rearrangements have resulted in an expressed gene that encodes a functional TCR or Ig subunit, i.e., a subunit that is not prematurely terminated during biosynthesis because the reading frame has been altered, or a stop codon has been introduced into the reading frame, by the V-D-J joining events (large subunit) or V-J joining events (small subunit), and/or somatic mutation. Although the variable region of TCR subunits varies from T cell to T cell, the constant region remains the same. Thus, determination of the amino acid sequence of the variable regions of TCRα and TCRβ subunits, in combination with the known amino acid sequence of the constant regions of the subunits, defines a unique functional TCR molecule. Kappler, J., et al., *Cell* 35: 295–302 (1983); Sim, G. K., et al., *Nature* 312: 771–775 (1984); Acuto, O., and Reinherz, E. L., *New England J. Med.* 312: 1100–111 (1985); Yague, J., et al., *Nucl. Acids Res.* 16: 11355–11364 (1988).

Analysis of the DNA sequences encoding the variable regions of the subunits of TCR from R28 reveals that the TCRα variable sequence is Vα1-derived, and the TCRβ variable sequence is Vβ6-derived (FIG. 1, Panels A and B). The unique amino acid sequences of the TCRα, [SEQ ID No. 5] and TCRβ [SEQ ID No. 7] variable regions are useful for designing therapeutic compositions (see below). Equivalents to the DNA sequences encoding the amino acid sequence of the variable regions of R28 TCR subunits [SEQ ID Nos. 4 and 6] are produced by substituting codons that are equivalent, i.e., that encode the same amino acid residues as each other, according to the standard genetic code (Table 2).

Structure of the Transgenes

Two DNA fragments, from plasmids paKRN and pbKRN, were used to generate the KRN transgenic line. Both plasmids contain DNA sequences initially derived from hybridoma R28. Peccoud, J., et al., *EMBO Journal* 9: 4215–4223 (1990). The functionally rearranged variable and joining regions of both the α and β chains of the TCR were inserted into appropriate sites of cassette vectors which are designed so as allow for the proper insertion of functionally rearranged TCR variable regions into TCR subunit genes which are operably linked to murine expression sequences upon introduction into transgenic mice.

The structures of the resulting plasmids, paKRN and pbKRN, are shown in FIGS. 1A and 1B, respectively, along with the exact nucleotide sequences of the functionally rearranged gene fragments that encode the variable region of each TCR subunit. Each plasmid contains DNA sequences coding for a specific TCR subunit and signals required for the expression of the coding sequences in mice. The gene for the α subunit is contained on paKRN; pbKRN comprises the gene for the β subunit. Specifically, paKRN contains the TCR Vet promoter region, an exon encoding the Vα4 variable region and joining segments isolated from R28, an intron which is absent in mature mRNA, an exon encoding the Cα constant region, and 3' flanking DNA sequences including polyadenylation and other 3' expression signals. Plasmid pbKRN has basically the same structure, and contains the TCR Vβ promoter region, an exon encoding the Vβ6 variable region and joining segments isolated from R28, an intron which is absent in mature mRNA, an exon encoding the Cβ constant region, and 3' flanking sequences including polyadenylation and other 3' expression signals.

Plasmids paKRN and pbKRN were deposited under the Budapest Treaty with the Collection Nationale de Culture de Micro-organismes (CNCM) of the Institut Pasteur, 28, Rue du Dr Roux, 75724 Paris Cédex 15, France, on May 18, 1994, and assigned the accession numbers I 1413 and I-1414, respectively. After issuance of a patent on this application, the CNCM will make the plasmids available to requestors in accordance with the Budapest Treaty and applicable U.S. patent laws and regulations. These deposits are not a license to practice the invention, and no admission is intended to be made that the deposits were necessary to satisfy the patent laws of the U.S. or any other country.

Example 2

Construction of a Transgenic TCR Mouse Line

This example describes the construction of transgenic mice that have TCR populations that consist substantially of the TCRα and TCRβ subunits encoded by the KRN transgenic allele. The KRN transgenic mice have a functionally viable, albeit limited, TCR repertoire.

Introduction of the Transgenes into the Murine Genome

In order to generate DNA molecules suitable for use in microinjection, it was necessary to eliminate the DNA sequences of paKRN and pbKRN required solely for the maintenance of these plasmids in prokaryotic host cells. This was accomplished by treating the plasmids with the restriction endonuclease SalI (paKRN) or KpnI (pbKRN) and isolating the relevant SalI or KpnI restriction fragment, respectively (see FIG. 1), by preparative agarose gel electrophoresis and electroelution. The restriction fragments were extracted twice with phenol-chloroform, precipitated with ethanol, and resuspended.

Isolated restriction fragments containing the TCRα and TCRβ transgenes were injected into B6×SJL F2 embryos according to standard procedures of transgenesis. Hogan, B., et al., *Manipulating the Mouse Embryo*, Cold Spring Harbor Laboratory Press, Cold Spring Harbor, N.Y., pages 1–332 (1986). Fertilized mouse eggs were recovered in cumulus from the oviducts of superovulated B6×SJL F1 females that had mated with males several hours earlier. The TCRα and TCRβ transgenes were injected in the most accessible pronucleus of each fertilized egg. Microinjected eggs were implanted into the oviducts of one-day pseudopregnant Swiss foster mothers and carried to term.

Several weeks after birth, a transgenic founder was identified by Southern hybridization with DNA molecules isolated from tail biopsies of the pups. The founder mouse possesses a genome which contains integrated copies of genes for both the TCRα and TCRβ subunits, and was crossed to C57B1/6 mice to establish the KRN transgenic mouse line.

Transmission of Transgenes

Mendelian transmission of a transgene is accomplished by crossing a transgenic mouse with a non-transgenic mouse. Typically, backcrosses are with C57B1/6 mice, but other strains are used. Transgene-positive offsprings are routinely identified by cytofluorimetric analysis of peripheral blood lymphocytes with reagents directed against the V/56 segment (see below), or by a nucleic acid hybridization assay. The hybridization assay includes the steps of obtaining a biological sample from each littermate, typically by physically separating the terminal 0.5 to 1.0 centimeters of the tail of the mouse, homogenizing or extracting the tail sample, purifying or amplifying DNA molecules therefrom, digesting the resultant DNA molecules with EcoRV restriction endonuclease, electrophoretically separating the restricted DNA sequences, transferring and binding the restricted, separated DNA sequences to a filter and hybridizing the filter-bound DNA sequences with a detectably labeled nucleic acid probe consisting of the approximately 0.7 kb XmaI-NotI fragment from paKRN (FIG. 1A). Additionally or alternatively, the approximately 0.5 kb XhoI restriction fragment from pbKRN can be detectably labeled and used as a probe for transgenic offspring.

Figure 2:
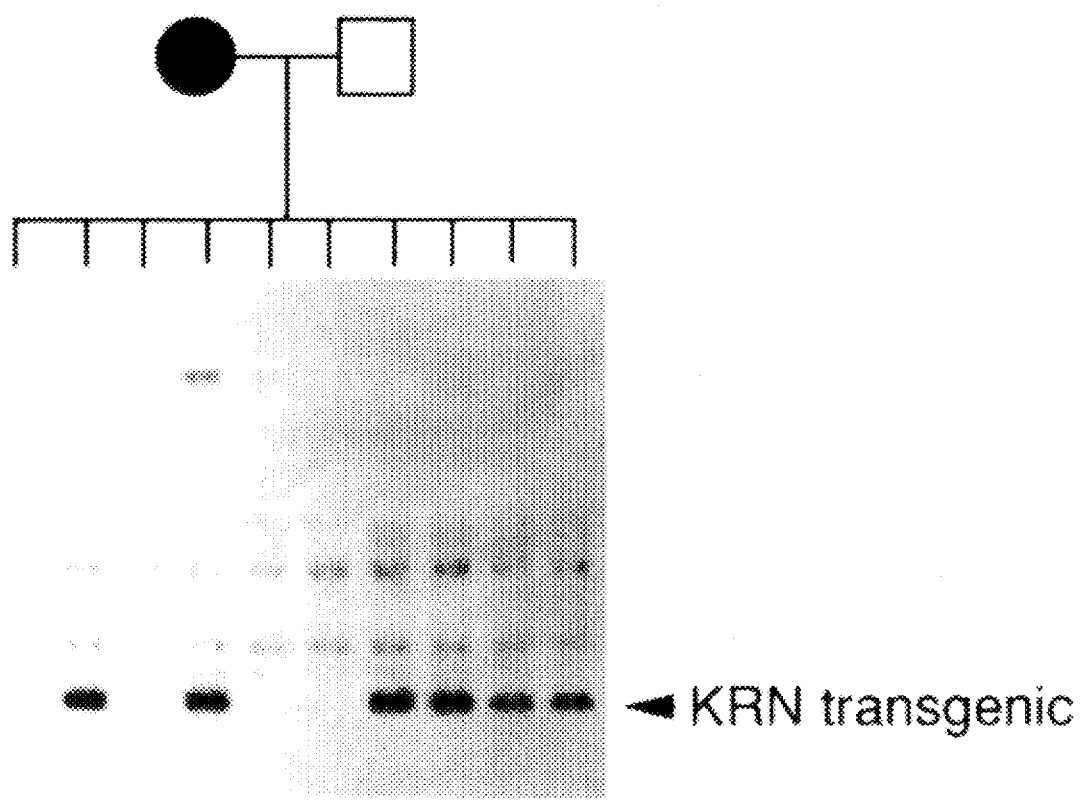
FIG. 2 depicts a nucleic acid hybridization ("Southern") assay for presence of DNA sequences of the KRN transgenic allele among offspring produced from a cross of KRN transgenic animal with a non-transgenic animal. A KRN transgenic female (filled circle) was crossed with a non-transgenic male (empty square), and DNA samples isolated from the tails of resulting progeny were probed with detectably-labelled transgene-specific DNA sequences.
Figure 3A:
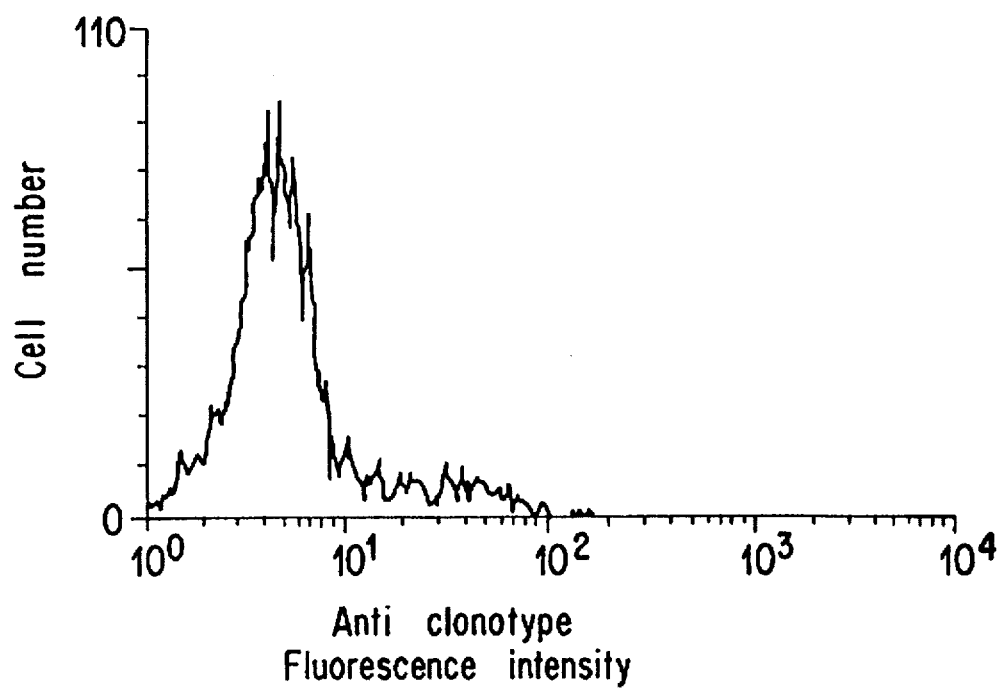
FIGS. 3(A–D) compares the results of cytofluorimetric analyses of the expression of T cell receptors in a wildtype mouse (left) with results obtained from examination of a KRN transgenic mouse (right).
Figure 3B:
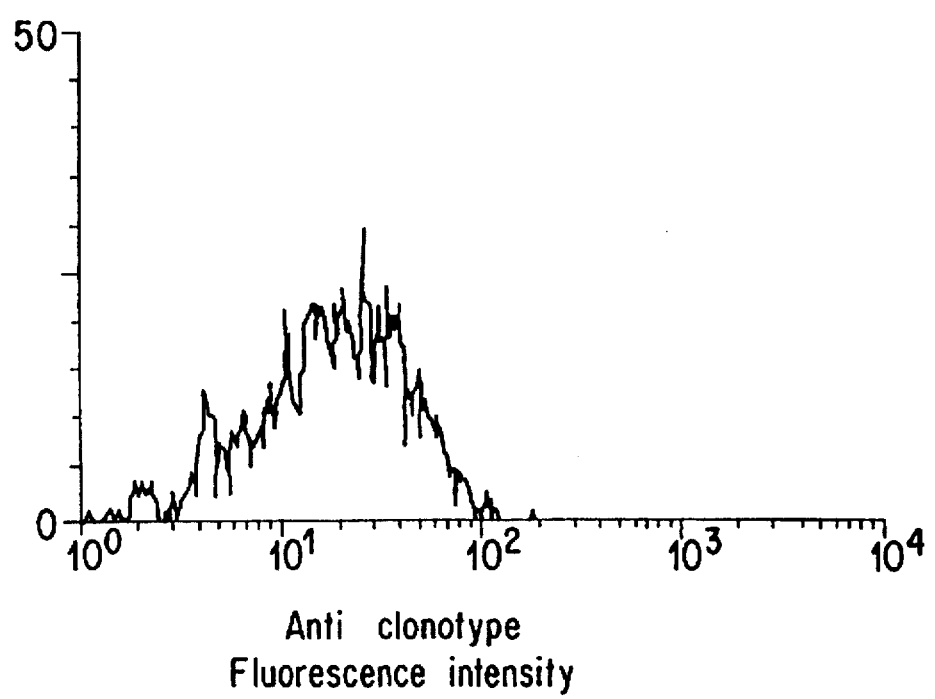
Figure 3C:
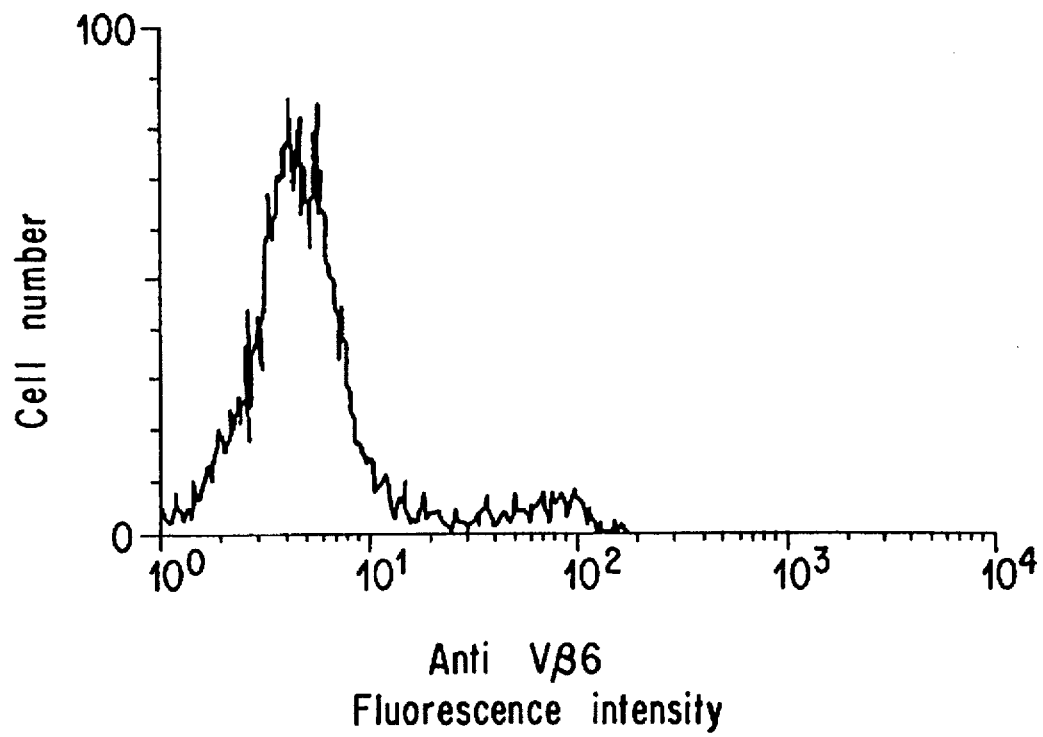
Figure 3D:
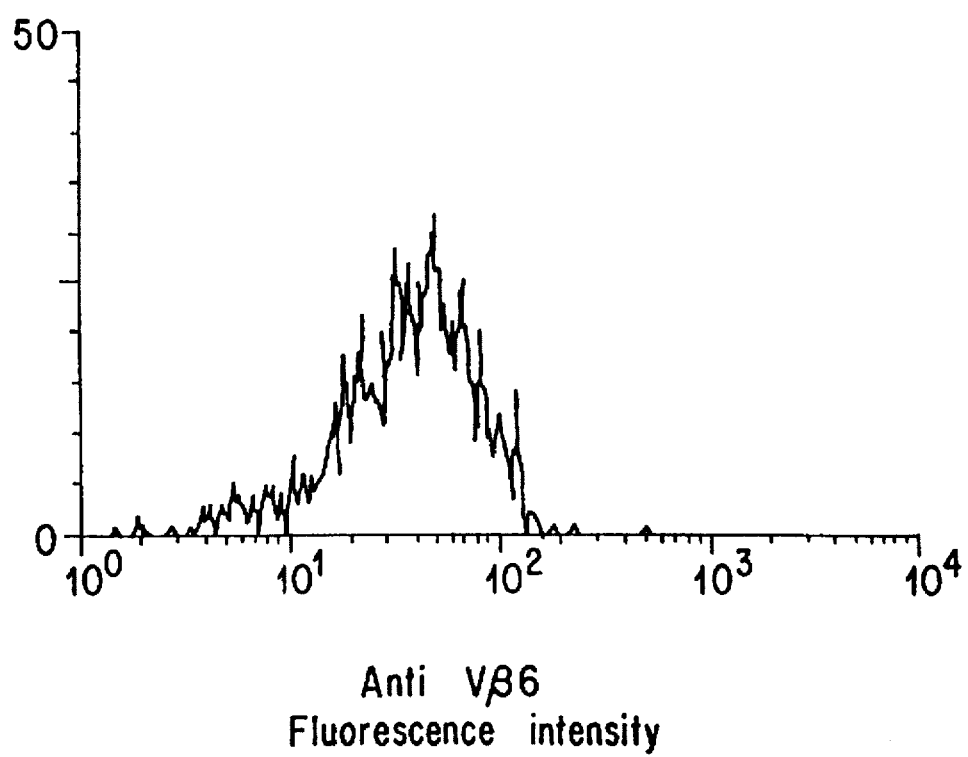

A representative example of a hybridization assay of a litter of KRN offspring is shown in FIG. 2. Transmission of the transgene is Mendelian; half the offspring are positive for the transgene. The α and β transgenes are closely linked on a mouse chromosome and appear to have co-integrated after micro-injection of the respective transgenic DNA sequences. The chromosomal locus comprising the TCR α and β transgenes is referred to as the KRN transgenic allele.

Expression of the KRN Transgenic Allele

Several lines of evidence indicate that both the α and β transgenes are expressed in a large proportion of lymphocytes in the transgenic mice, and that T cell receptors composed of the transgenitally encoded TCR subunits are the predominate members of a limited TCR repertoire in the transgenic animals.

Expression of TCRα. Expression of the TCR α subunit encoded by the transgene was demonstrated by two methods.

First, TCRα transcripts from lymph node cells were amplified en masse via PCR reactions that use degenerate oligonucleotides in order to achieve random sampling of the TCRα repertoire. Candéais, S., et al., *Proc. Natl. Acad. Sci. (USA)* 88: 6167–6170 (1991). PCR products corresponding to amplified transcripts were cloned into an M13 bacteriophage vector, and plaques containing cDNA sequences corresponding to TCRα subunits were revealed by hybridization with a detectably labeled nucleic acid Cα-specific probe comprising DNA sequences from the shared Cα constant region, i.e.,

TTTGTTGGTATTGGAAGGGGCCAGAGCAC
AGAAGTACACG    [SEQ ID NO. 8].

Among TCRα cDNA clones, clones corresponding to transgene-encoded transcripts were detected by hybridization with a detectably labeled nucleic acid transgene-specific probe, consisting of the approximately 0.7 kb XmaI-NotI fragment from paKRN (FIG. 1A) and corresponding to the functionally rearranged V-J joining region contained in paKRN, which specifically hybridizes to cDNA sequences derived from the transgene encoded TCRα variable region. Of the clones that were detected by hybridization with the Cα-specific probe, 97% were also detected by hybridization with the transgene-specific probe. This result indicates that mRNA sequences corresponding to the transgene encoded TCRα subunit account for the vast majority of TCRα transcripts in the transgenic animals.

Second, an anti-idiotypic serum was raised in normal mice by immunization with transgenic lymph node cells. The anti-idiotypic serum contains polyclonal antibodies that recognize an epitope found in or near the variable region of the predominant TCRs from KRN transgenic mice.

The specificity of the anti-idiotypic serum for the TCR of hybridoma R28 was verified by demonstrating that it specifically recognized and stained T hybridomas and transfected cells expressing the TCR α and β chains from R28, or other T cells, e.g., KLy 11.10, Tris and BDC2.5. $CD4^+$ lymphocytes were isolated from wildtype and KRN transgenic mice according to standard methods. Wysocki, L. J., and Sato, V. L., *Proc. Natl. Acad. Sci. (USA)* 75: 2844–2848 (1978); Wasik, M. A., and Morimoto, C., *J. Immunol.* 144: 3334–3340 (1990); Harriman, G. R., et al., *J. Immunol.* 145: 4206–2414 (1990); Koulova, L., et al., *J. Immunol.* 145: 2035–2043 (1990). $CD4^+$ lymphocytes were incubated with a saturating dose of anti-idiotypic sera at 4° C. for 15 minutes, washed, and incubated with detectably labeled (i.e., fluorescently tagged by conjugation to FITC) goat anti-mouse antibodies for 45 minutes at 4° C. After washing, the cells were fixed with 1% formaldehyde and analyzed by passage through a fluorescence-activated automatic cell sorter (e.g., a Beeton-Dickinson FACScan®). Kung, P. C., and Goldstein, G., U.S. Pat. Nos. 4,381,295 (Apr. 26, 1983), 4,364,932 and 4,364,936 (both Dec. 21, 1982). The cytofluorimetric analysis indicates that the anti-idiotypic serum reacts with a majority of CD4$^+$ lymphocytes in transgenic mice, but does reacts with CD4$^+$ lymphocytes from control animals with only low intensity (FIG. 3, Panel A).

Expression of TCRβ. Expression of TCRβ chain transgene in KRN mice was verified by cytofluorimetric analysis of CD4$^+$ lymphocytes. The RR4.7 monoclonal antibody (commercially available from Pharmingen, San Diego, Calif.; catalog No. 01361C), which recognizes the amino acid sequence encoded by the V gene segment (Vβ6) present in the functionally rearranged TCRβ of the transgene, was used. As indicated by reaction with the RR4.7 monoclonal antibody, Vβ6 was present on essentially all CD4$^+$ lymphocytes in transgenic mice (FIG. 3, Panel B). This assay can be used to identify transgene-positive animals in mixed litters.

The antigen specificity imparted by TCRs composed, of the α and β chains of the R28 TCR could be detected in peripheral lymph node cells. Strong proliferation of cells was detected when lymph node T cells were incubated in the presence of the BPR-derived oligopeptide having the amino acid sequence Lys-Pro-Val-Asn-Thr-Phe-Val-His-Glu-Ser-Leu-Ala- Asp-Val-Gln-Ala-Val-Cys-Ser-Gln-Lys  [SEQ ID NO. 1]

and APCs expressing MHC molecules.

Example 3

Isolation and Characterization of Transgenic Arthritic Mice

The new transgenic model of arthritis describe herein did not result from a directed effort towards this goal. The KRN line of transgenic mice was constructed by introducing into mice the genes encoding the α and β subunits of the T cell receptor for antigen (TCR) from a murine T cell hybridoma reactive to bovine pancreatic RNAase, in order to address questions of fundamental immunology pertaining to the selection of the T cell repertoire. In the genetic background of the strain of mice into which the KRN transgene was initially introduced, C57B1/6, the transgene did not confer an abnormal phenotype. Of course, due to their limited TCR repertoires, these mice may have a reduced ability to mount appropriate immune responses against pathogens that are, in any event, less frequently encountered in the laboratory environment.

Figure 5:
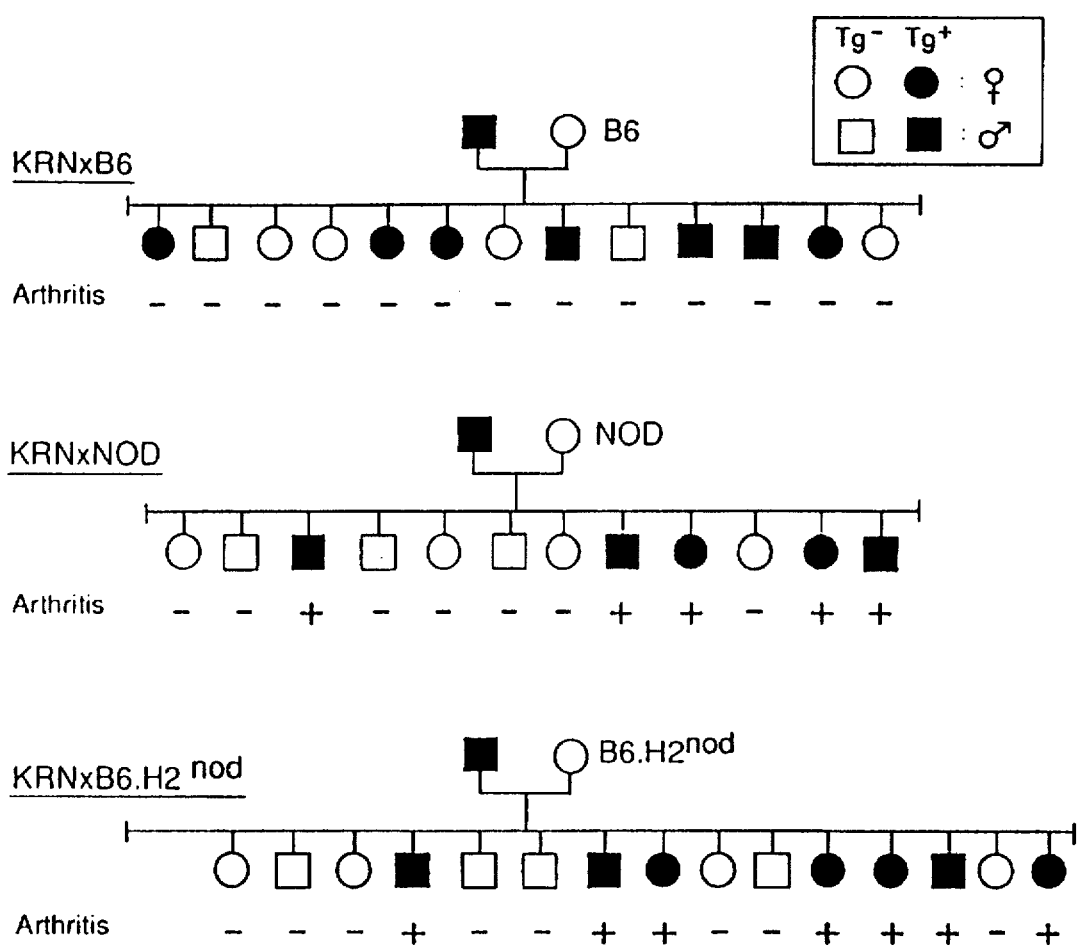
FIG. 5 demonstrates the arthritic phenotype induced by the KRN transgenic allele in different genetic backgrounds. Three crosses are shown; in each case a male KRN transgenic animal (filled squares) derived from the B6 strain of mice was crossed with a non-transgenic female animal (open circles) of various strain backgrounds. In the cross diagrammed in the Top Panel of FIG. 5, the non-transgenic female animal is from the B6 strain of mice, and no arthritis is observed in the offspring. In the cross shown in the Middle Panel of FIG. 5, the non-transgenic female animal is from the NOD strain of mice, and complete penetrance of the arthritic phenotype occurs, evidenced by the fact that all transgenic offspring develop arthritis. In the cross shown in the Bottom Panel of FIG. 5, complete penetrance of the arthritic phenotype is also seen when the non-transgenic female animal has a cogenic genome which includes the MHC loci of the NOD strain (B6.H2$^{nod}$).

The C57B1/6 KRN-transgenic mice were then adventitiously crossed with inbred mice of the NOD strain. Surprisingly, all of the transgene-positive offspring from this cross develop severe symptoms associated with RA in humans, i.e., chronic inflammation and deformation of the limb joints. There is a 100% penetrance of the disease in NOD KRN-transgenic animals, i.e., every NOD mouse that inherits the KRN transgenic allele develops arthritis, as shown in FIG. 5. Males are affected as well as females. There is no arthritis when the transgenic mice are not of the NOD background (FIG. 5, KRN×B6), and such mice are used as transgenic maintenance animals.

Clinical Course of Arthritis

Figure 4A:
FIGS. 4(A–B) shows the clinical manifestations of arthritis in transgenic arthritic mice and the course of development of arthritis therein. In Panel A of FIG. 4, the hind limb of a transgenic KRN×NOD arthritic mouse is shown adjacent to the hind limb of a non-transgenic littermate. Panel B of FIG. 4 is a chart displaying the results of chronological measurements of ankle thickness of transgenic KRN×NOD arthritic mice and their non-transgenic littermates.
Figure 4B:
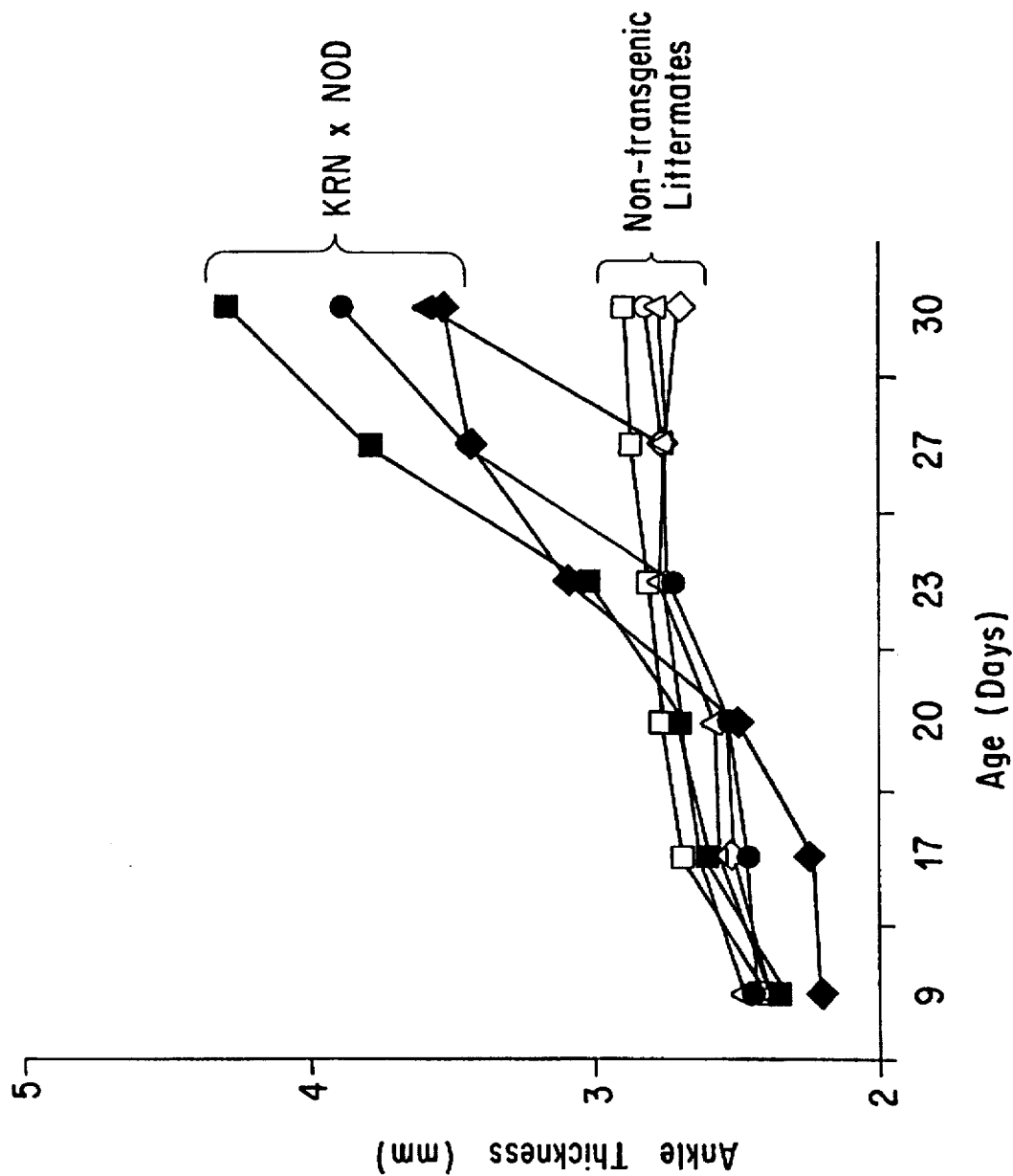

The progression of arthritis in mice carrying the KRN transgene and NOD-derived MHC genes required for penetrance of the arthritic genotype (see below) was followed by calliper measurements of the thickness of the ankle joints of arthritic animals, a simple assay which gives measurements that correlate well with the onset and evolution of the inflammatory process. Transgenic arthritic mice show signs of joint inflammation, with a sharp onset between three and four weeks of age; no clinical signs are apparent before that time (FIG. 4B). The distal joints appear more affected than the knee or elbow. The joints are swollen and red; deformation sets in after a few weeks, with the expected consequence that limb motility is reduced (see FIG. 4A). This state persists for several weeks. After ten to twelve weeks, the inflammatory symptoms tend to subside somewhat, but major sequellar deformations persist.

Because of the serious reduction in motility that their arthritis imparts, NOD KRN-transgenic mice are poor breeders. However, litters from NOD KRN-transgenic parents are obtainable. In practice, arthritic animals are generated by maintaining the KRN transgene in mice of the C57B1/6 background, wherein arthritic symptoms are not manifested, and crossing transgene positive mice with NOD mice. All KRN transgene-positive offspring animals which result from this cross develop arthritis and are identified prior to the onset of symptoms by nucleic acid hybridization or cytofluorimetric analysis.

Radiography

Figure 6A:
FIG. 6 contrasts a radiograph (X-ray image) of the hind limb of a transgenic KRN×NOD arthritic mouse (Right Panel) with a radiograph of the hind limb of a non-transgenic, non-arthritic littermate (Left Panel).
Figure 6B:

Radiography (x-ray imaging) was performed on individual NOD KRN-transgenic animals as well as non-transgenic littermates at various times after disease onset in the transgenic animals. Bone and cartilage erosion is clearly visible in the knee and ankle (FIG. 6), reflecting the gross deformations that are externally visible (compare with Panel A of FIG. 4). Osteosynthesis with osteophytosis is widespread. In older animals, there is considerable rearrangement of the joints, consistent with the deformations visible externally. The spinal column also appears somewhat affected in radiographs.

Histopathology

Joints from normal or arthritic (KRN-transgenic NOD) mice were examined by histological examination of decalcified paraffin sections of spine, knee or paw joints, after staining with hematoxylin-eosin according to standard and routine pathology techniques. Stevens, A., in Theory and Practice of Histological Techniques, Bancroft, J. D., and Stevens, A., eds., 3rd Ed., Churchill Livingstone, Edinburgh, N.Y., pp. 107–118 (1990). There are very obvious signs of joint inflammation in the transgenic arthritic mice that parallel developments in patients with RA: synovial hyperplasia with several superimposed layers of large synoviocytes, polymorphic cellular infiltration (granulocytes, lymphocytes, plasmocytes), fibrinous exudate in the joints. Cartilage erosion, destruction and resorption is prevalent after a few weeks of disease. Again, lesions are predominant in the distal joints, clear but less active in the knee, and very discrete in the hip. The spine is also affected by inflammatory infiltrates, but mildly. No histological lesions are present before three weeks of age.

It is important to note that signs of inflammation or infiltration have not been detected in any other organ examined. In sum, the autoimmune response in the transgenic arthritic mice is severe but, as in RA, is limited to synovial tissues, particularly cartilage. Thus, the transgenic arthritic animal model of the invention, unlike previously described animal models of RA, faithfully reproduces the distinguishing features of human RA.

Requirements for the KRN Phenotype

The initial observation of transgenic arthritis was made in F1 mice, originating from a cross between a mouse carrying the KRN transgenic allele in the C57B1/6 background and an inbred NOD/Lt mouse. The resultant KRN-transgenic NOD animals have mixed alleles at each genetic locus in their genomes, consisting of an equal contribution of alleles from both the NOD/Lt parent and the C57B1/6 parent. Since the KRN transgenic allele did not give rise to any arthritic symptoms when present in the C57B1/6 background, genetic elements (i.e., one or more alleles) derived from the NOD genome contribute to the induction of arthritis by the KRN transgenic allele.

In order to identify the required NOD allele(s), non-NOD KRN-transgenic mice were crossed with mice of the B6.NH-$2^{nod}$ strain (gift of Dr. H. Kikutani). The B6.NH-$2^{nod}$ strain is a chimeric strain derived from the NOD and B6 strains of mice. In B6.NH-$2^{nod}$ mice, all genetic loci have the same alleles as B6, except for the MHC locus, which is derived from the NOD strain of mice. Arthritic disease was manifested in the progeny from the cross of non-NOD KRN-transgenic and B6.NH-$2^{nod}$ mice, with the same prevalence and characteristics as in a control cross of KRN-transgenic and NOD mice (FIG. 5, KRN×B6.NH-$2^{nod}$ and KRN×NOD, respectively). In contrast, offspring of a cross between KRN-transgenic mice and B6 mice were not arthritic (FIG. 5, KRN×B6), and there was no arthritic disease in other genetic combinations tested (i.e., in crosses of KRN-transgenic mice from B10.D2, B10.M, B10.S, B10.BR, B10.A, and B10.A(4R) strains).

Thus, arthritic disease resulting from the KRN transgenic allele is fully manifested due to genetic elements provided by particular MHC loci of different strains of mice. In particular, the MHC locus of the NOD strain of mice results in full manifestation of the KRN phenotype. MHC loci from other strains of mice, or MHC loci from other animals including humans, are testable in the mouse model for their ability to enable the KRN phenotype (see below). Thus, the invention provides a method for identifying and isolating additional, non-NOD derived MHC loci that can be used to practice the invention.

Immunology of the Transgenic Arthritic Mice

The very nature of the transgenic allele which directs arthritis in KRN-transgenic NOD mice implies a determining role of T lymphocytes in the disease and, by extension by analogy, in PA. Indeed, extensive clonal deletion of the central and peripheral T cell populations of the transgenic arthritic mice occurs during development of the animals. The mechanism of clonal deletion is very active around birth; few, if any, CD4$^+$ and CD8$^+$ T cells are present in the peripheral lymphoid organs at that time. The depletion of T cells tends to abate somewhat with age, and CD4$^+$ lymphocytes appear in animals of about three weeks of age in the spleen and lymph nodes.

The B cell component of the immune system of transgenic arthritic mice is less affected, with relatively normal numbers and distribution of B cells. However, there is an imbalance in the isotype of circulating IgG, with a marked increase of the IgG1 isotype in KRN-transgenic NOD mice. Rheumatoid factors (i.e., antibodies to the constant region of IgG antibodies) have not been detected in the transgenic arthritic mice. However, after two or three months, the spleen and lymph nodes of many KRN-transgenic NOD mice are grossly enlarged, presumably in response to the constant inflammatory state of the animal.

Example 4

Methods of Evaluating Anti-Arthritic Compositions

Because of the reliable and reproducible nature of arthritis in the transgenic arthritic mice of the invention, and its clear relationship to human rheumatoid arthritis, the transgenic animals of the invention are used to estimate the safety and efficacy of anti-arthritis compositions under development. Anti-arthritic compositions are administered prior to the onset of clinical manifestations, or after the disease has set in but before irremediable joint destruction and deformation have taken place.

Therapeutic Immunointervention

Figure 7:
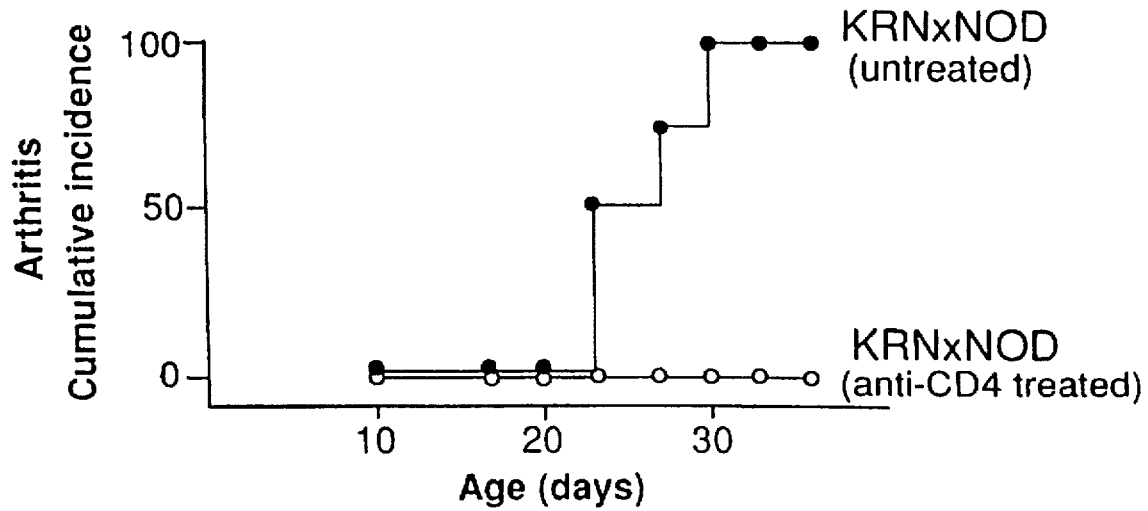
FIG. 7 shows the effect of anti-CD4 monoclonal antibody in preventing the occurrence of arthritis in transgenic arthritic mice, compared to the occurrence of arthritis in untreated control transgenic arthritic mice. The progress of arthritis was determined by clinical examination of the animals every third day.

KRN-transgenic NOD arthritic mice were treated with anti-CD4 antibody, a composition that has shown some promise in alleviating the symptoms of RA in humans. Moreland, L. W., et al., *Arthritis Rheum.* 36: 307–319 (1993). The progress of arthritis in the treated animals, and in untreated control animals, was monitored by clinically examining the mice every third day. As shown in FIG. 7, treatment of transgenic arthritic mice with anti-CD4 antibody from two weeks of age prevented the appearance of pathological manifestations.

The animal model of the invention is used to evaluate other potential anti-arthritic compositions, including but not limited to glucocorticoids, lymphokines, interferons, conjugates of cytotoxins with antibodies, CD proteins, MHC proteins, derivatives of CD and MHC proteins, and synthetic compounds or isolated effector biomolecules that influence antigen presentation by MHC molecules, TCR recognition of MHC-presented antigens, and/or interactions between MHC molecules and CD proteins. Because the transgenic arthritic animals of the invention develop arthritic symptoms in a predictable fashion, various effects of anti-arthritic compositions tested in the animal model of the invention can be examined in more rigorous fashion than was previously possible.

Anti-arthritic compositions can achieve their effect by preventing inflammation, by limiting the inflammatory response, or by limiting the destruction of tissue that occurs subsequent to inflammation. Administering an anti-arthritic composition to the transgenic animals of the invention at defined postnatal timepoints reveals if the composition exerts its effect at an early or late stage of arthritis. For example, anti-arthritic compositions that prevent inflammation will not be effective if administered after the inflammatory response has initiated, unlike anti-arthritic compositions that prevent sequellar destruction of tissue.

The potency of anti-arthritic compositions is evaluated in terms of causing a statistically significant delay in the time of onset and/or the extent of inflammation and/or irremediable joint destruction and limb deformation in the transgenic arthritic animals of the invention. Changes in cellular immunological parameters of the transgenic arthritic animals of the invention, e.g., the number and distribution of CD4$^+$ or CD8$^+$ cells or of particular TCR or Ig molecules, in response to anti-arthritic compositions are determined to elucidate underlying mechanisms of therapeutic immunointervention.

Genetic Therapy

Transgenes comprising DNA sequences encoding potentially anti-arthritic gene products, including polypeptides, are introduced into the genome of a mouse. Candidate anti-arthritic transgenes are introduced into the transgenic arthritic animal model of the invention by mating an offspring of the anti-arthritic transgenic founder animal with transgenic arthritic mice treated with anti-CD4, or another anti-arthritic agent, thereby imparting the transgenic arthritic mice sufficient mobility to undertake the mating process with vigor. Alternatively, candidate anti-arthritic transgenes are introduced into the genomes of individuals from the NOD strain of mice, and an offspring of the NOD founder is mated with a non-arthritic KRN-transgenic mouse and the development of arthritic symptoms in singly- and doubly-transgenic offspring is monitored and compared. An anti-arthritic DNA sequence is one which, when expressed in a transgenic arthritic animal that develops arthritis in the absence of the anti-arthritic DNA sequence, results in reduced, delayed or no inflammation or which limits or eliminates sequellar destruction of tissue subsequent to inflammation.

Example 5

Methods of Evaluating Arthritogenic Compositions

In KRN transgenic mice with an MHC locus from the NOD strain of mice, all transgenic mice develop arthritis. KRN transgenic mice with an MHC locus from strains of mice in which the KRN transgenic allele fails to induce arthritis are used to evaluate compositions for their arthritogenic potential. Compositions which enhance the arthritic potential of the KRN transgenic allele are arthritogenic in the animal model of the invention. Such compositions include but are not limited to glucocorticoids, lymphokines, interferons, conjugates of cytotoxins with antibodies, CD proteins, MHC proteins, derivatives of CD and MHC proteins, and synthetic compounds or isolated effector biomolecules that influence antigen presentation by MHC molecules, TCR recognition of MHC-presented antigens, and/or interactions between MHC molecules and CD proteins. Isolated effector biomolecules (e.g., γ-interferon) that may be more prevalent in human females, and which have thus been suggested to be related to the increased incidence of RA therein (Fox, H. S., et al., *J. Immunol.* 146: 4362–4367 (1991)), are tested in both male and female transgenic non-human animals of the invention in order to eliminate effects due to other gender differences.

Arthritogenic compositions also include transgenes encoding an MHC protein, wherein DNA sequences expressed by the transgenes are derived from the MHC loci of animals including humans. Some MHC proteins influence the occurrence of autoimmune disease, and specific variant MHC alleles have been demonstrated to be correlated with a higher risk of certain human autoimmune diseases. In humans, wherein MHC antigens are known as HLA (human lymphocyte antigen) proteins, for example, individuals with the HLA-DR4 allele are six times more likely than those with other HLA variants to acquire rheumatoid arthritis. Steinman, L., *Sci. American* 269: 106–114 (1993). Yersinia arthritis and ankylosing spondylitis are highly correlated with the HLA-B27 allele. Vaughan, J. H., in *Immunological Diseases, Vol. II*, 3rd Ed., Samter, M., ed., Little, Brown and Company, pages 1029–1037 (1978).

As demonstrated by experiments with transgenic mice, the mouse T cell repertoire is perfectly capable of using human MHC gene products (HLA proteins). Kievits, F., et al., *Nature* 329: 447–449 (1987). DNA sequences encoding particular HLA molecules from humans are isolated and genetically engineered so as to be capable of introduction into the mouse genome and expression in murine cells. Utilization of human MHC gene products in mice requires the concomitant presence of $\beta_2$-microglobulin protein molecules; accordingly, DNA sequences encoding human $\beta_2$-microglobulin are similarly genetically engineered. Kievits, F., et al., *Nature* 329: 447–449 (1987). The transgenes are introduced into the genome of a mouse, and an offspring of a doubly transgenic (MHC and $\beta_2$-microglobulin) founder is mated with a non-arthritic KRN-transgenic mouse. Doubly-transgenic (MHC and $\beta_2$-microglobulin) and triply-transgenic (MHC, $\beta_2$-microglobulin and KRN) offspring are identified via the hybridization assay described above, using probes derived from the DNA sequences of the MHC, $\beta_2$-microglobulin and KRN transgenes. The occurrence and development of arthritic symptoms in triply-transgenic offspring is monitored and compared to that of doubly- and non-transgenic littermates.

An arthritogenic DNA sequence is one which, when expressed in a transgenic arthritic animal that does not develop arthritis in the absence of the arthritogenic DNA sequence, results in partial or full manifestation of the KRN phenotype. DNA sequences that are testable by the method of the invention include but are not limited to those of human HLA-B27, HLA-DR4 and other genes encoding human MHC proteins (in conjunction with transgenes encoding human $\beta_2$-microglobulin) (Kievits, F., et al., *Nature* 329: 447–449 (1987)), and MHC alleles from animals for which guarantees of prolonged mobility are sought (e.g., racehorses) in conjunction with $\beta_2$-microglobulin genes appropriate for the species of animal contributing the MHC allele to be tested. The animal model of the invention provides a basis to determine underlying cellular and molecular mechanisms of observed correlations between particular MHC alleles and various forms of human arthritis. For example, the human MHC protein encoded by HLA-B27 is associated with some types of arthritis in humans (Vaughns, supra) and, when transgenitally expressed in mice, is able to display antigens to murine TCRs (Kievits et al., supra). This approach is more satisfying, at least in the mechanistic sense, than determining correlations between particular human MHC alleles and arthritic diseases.

The potency of arthritogenic compositions is evaluated in terms of causing a statistically significant advancement in the time of onset of arthritis and/or increase in the extent of inflammation and/or irremediable joint destruction and limb deformation in the transgenic arthritic animals of the invention. Alternatively or additionally, the potency of arthritogenic compositions is evaluated in terms of a statistically significant increase in the incidence of arthritis or arthritic symptoms in the KRN-transgenic non-arthritic animals of the invention. Changes in cellular immunological parameters of the transgenic animals of the invention, e.g., the number and distribution of CD4$^+$ or CD8$^+$ cells or of particular TCR or Ig molecules, in response to arthritogenic compositions are determined to elucidate underlying mechanisms of therapeutic immunointervention.

Example 6

Isolation of Immune System Components that Bind Endogenous Polypeptidic Arthritogenic Self Antigens This example describes methods of isolating polypeptide antigens that are recognized by transgene encoded TCRs in the transgenic arthritic mice of the invention. These polypeptides are used to isolate cells and effector biomolecules from the immune systems of the transgenic arthritic animals of the invention that specifically bind one or more epitopes of murine proteins comprising polypeptide arthritogenic selfantigens (PASAs). The isolated cells and effector biomolecules are used to isolate PASA-comprising proteins from other species of animals including humans (Example 7).

Oligopeptides Presented by APCs in Arthritic Animals. A prerequisite for the subsequent examples is the identification of endogenous polypeptide antigens that are presented to the transgene encoded TCR of the invention during the etiology of arthritis. To this end, antigen presenting cells (APCs) are isolated from transgenic arthritic mice at various times before and during the development of arthritic symptoms. Of particular interest are APCs present in the thymus during the active period of clonal deletion around birth, however, APCs are also isolated from other tissues and at other times during the life of the mice. Heparinized venous blood is obtained from the transgenic arthritic mice of the invention, and polymorphonuclear blood cells (PMBCs) are isolated therefrom by, e.g., Ficoll-Hyapque density gradient centrifugation. Preparations of PMBC are depleted of monocytes and/or macrophages by plastic adherence for 2 hours at 37° C. in tissue-culture flasks. Adherent cells are recovered by scraping, resuspended in an appropriate buffered media which does not include fetal calf serum (FCS) as fetal calf serum contains antigen(s) which can be recognized by the TCR of R28. Dellabona, P., et al., Eur. J. Immunol. 21: 209-213 (1991). The resuspended cells are used a source of APCs. Koulova, L., et al., J. Immunol. 145: 2035-2043 (1990).

APCs are treated with 0.025% trypsin to enhance the harvest of oligopeptides. Oligopeptides associated with MHC molecules are isolated according to the method of Slingluff, C. L., et al., J. Immunol. 150: 2955-2963 (1993), and fractionated by reversed phase high pressure liquid chromatography (HPLC), although other separation techniques may be used. Lehninger, A. L., Biochemistry, 2d Ed., pp.95-121. HPLC fractions containing relevant peptides are identified by activation of R28 hybridoma cells, as measured by the production of interleukin-2, in the presence of APCs isolated from non-arthritic NOD mice. Miedema, F., and Melief, C. J. M., Immunol. Today 6: 258-259 (1985). HPLC fractions containing activity are pooled and rechromatographed as required in order to generate fractions of sufficient purity for subsequent uses intended. However, even relatively crude fractions suffice to identify hybriodmas producing effector biomolecules specific for endogenous polypeptide arthritogenic self antigens (PASAs).

If sufficient homogenous material is generated, then the oligopeptides of R28-stimulatory HPLC fractions are sequenced by standard methods, including but not limited to repetitive Edman degradation. Lehninger, A. L., Biochemistry, 2d Ed., pp.95-121 (1978). Alternatively, tandem mass spectrometry (TMS) is used to identify the sequences of the most abundant peptides. Cox, A. L., et al., Science 264: 716-719 (1994). Although TMS cannot distinguish between Ile and Leu amino acid residues in a polypeptide, TMS generates amino acid sequence data that can be used to design pairs of oligopeptides alternately comprising Ile or Leu. Oligopeptides comprising TMS-derived amino acid sequences are chemically synthesized according to standard methods (Stewart and Young, Solid Phase Peptide Synthesis, Pierce Chemical Co., Rockland, Ill. (1985)) and purified from reaction mixtures by reversed phase HPLC. Isolated synthetic oligopeptides are tested for their ability to stimulate the R28 hybridoma in the presence of APCs isolated from non-transgenic NOD mice, and in this manner the sequences of actual R28-stimulatory oligopeptides are determined. These amino acid sequences correspond to short polypeptide fragments derived from endogenous PASA-comprising proteins.

Production of Hybridomas

The spleen and thymus are isolated post-mortem from an arthritic transgenic mouse (e.g., a KRN-transgenic NOD mouse). Lymphocytes (T or B cells) are prepared from the isolated spleens or thymus of one or more transgenic animals at various times during the development of arthritis. Individual antibody-producing T or B cells are fused in vitro with immortalizing cells. The resulting stably reproducing fused cell lines (hybridomas), each of which expresses TCRs (T cells) or antibodies (B cells) with a unique antigen-binding (variable) regions, are cultured by standard lymphocyte culturing techniques. Harlow, E., and Lane, D., Antibodies: A Laboratory Manual, Cold Spring Harbor Laboratories, Cold Spring Harbor, N.Y., pages 139-281 (1988); Ausubel, F. M., et al., Eds., Current Protocols in Molecular Biology, Vol. 2, Greene Publishing Associates and John Wiley & Sons, pages 11.4.1-11.11.5 (1993).

T cell hybridomas are screened for activation (measured as interleukin-2 secretion) by APCs prepared from NOD mice in the presence or absence of an oligopeptide corresponding to amino acids 41-61 of bovine pancreatic ribonuclease (BPR) and having the amino acid sequence Lys-Pro-Val-Asn-Thr-Phe-Val-His-Glu-Ser-Leu-Ala- Asp-Val-Gln-Ala-Val-Cys-Ser-Gln-Lys [SEQ ID NO. 1].

Alternatively, the T cell hybridomas are screened for activation in the presence of the BPR-derived oligopeptide and APCs displaying a wildtype or mutant $A^k$ MHC molecule due to transfection with a regulatable $A^k$ MHC gene. Dellabona, P., et al., Eur. J. Immunol. 21: 209-213 (1991). Either type of APC is alternatively used with crude or synthetic oligopeptides derived from PASA-comprising proteins (see above). In any event, R28 hybridoma cells are used as positive controls. The T cell hybridomas identified and isolated in this manner express TCR subunits which are either identical to those encoded by the transgenes of the invention, or mutants thereof produced in the transgenic arthritic mice and having altered binding characteristics.

B cell hybridomas are screened for the production of a monoclonal antibody that recognizes the BPR-derived oligopeptide and/or crude or synthetic oligopeptides derived from PASA-comprising proteins (see above). The desired B cell hybridomas are identified by ELISA assays using the BPR-derived oligopeptide and/or crude or synthetic oligopeptides derived from PASA-comprising proteins as antigen. Monoclonal antibodies produced by the identified hybridomas are purified if necessary. Harlow, E., and Lane, D., Antibodies: A Laboratory Manual, Cold Spring Harbor Laboratories, Cold Spring Harbor, N.Y., pages 139-281 (1988); Ausubel, F. M., et al., Eds., Current Protocols in Molecular Biology, Vol. 2, Greene Publishing Associates and John Wiley & Sons, pages 11.4.1-11.11.5 (1993).

Monospecific Antibodies

The crude or synthetic oligopeptides derived from endogenous PASA-comprising proteins (see above) are used to generate monospecific antibodies that are used in subsequent examples.

A "polyclonal antibody" refers to a composition that comprises an assortment of different antibodies that all recognize a particular antigen. Although useful in a variety of ways, polyclonal antibodies suffer from limitations due to their heterologous composition. For example, cross-reactivities of some polyclonal antibodies to antigens other than the one used to induce an immune response are commonly observed. The specificity of a polyclonal antibody can be limited to a particular epitope by using an isolated or synthetic antigen or hapten corresponding to a single chosen epitope. The antigen, or the hapten in association with a carrier, is used to generate a humoral immune response in an animal. The polyclonal antibody that results is specific for the chosen epitope and is referred to as a "monospecific antibody" or "antipeptide antibody." In particular, synthetic oligopeptides are used as antigens or haptens to generate monospecific antibodies that can be used to assay or isolate a protein comprising a sequence that corresponds with, or is similar to, the sequence of the oligopeptide.

The crude or synthetic oligopeptides derived from endogenous PASA-comprising proteins (see above) are used to generate monospecific antibodies according to standard methods. Wilkins, T. D., et al., U.S. Pat. No. 4,879,218 (Nov. 7, 1989); Harlow, E., and Lane, D., Antibodies: A Laboratory Manual, Cold Spring Harbor Laboratories, Cold Spring Harbor, N.Y., pages 53–137 (1988); Ausubel, F. M., et al., Eds., Current Protocols in Molecular Biology, Vol. 2, Greene Publishing Associates and John Wiley & Sons, pages 11.12.1–11.15.4 (1993).

Example 7

Isolation of Proteins Comprising Polypeptide Arthritogenic Self Antigens (PASAs)

During development of the transgenic arthritic mice of the invention, an initiating immunologic event triggers a cascade of immunologic events that culminates in the transgenic animals developing severe arthritic symptoms in a reproducible and thus predictable manner. Because the KRN transgenic allele results in a majority of T cells in an individual mouse having a specific TCR, and because antigen-presenting MHC proteins from particular strains of mice are required for the transgenic phenotype to be manifested, it is possible that an important immunologic event that occurs relatively early in arthritis is recognition of endogenous self antigens by T cells. These endogenous self antigens are generally referred to herein as endogenous polypeptide arthritogenic self antigens (PASAs). The murine protein comprising these PASAs is believed to correspond to a human protein of primordial importance in the genesis of human PA. Human PASA-comprising proteins, and synthetic and derivatized compounds derived from human PASA-comprising proteins, are useful in the diagnosis, prevention or therapy of arthritis in humans (see subsequent examples). The transgenic arthritic animals of the present invention provide the means by which PASA-comprising proteins, or DNA sequences encoding such proteins, may be isolated from many animal sources including humans.

Purification of PASA-Comprising Proteins by Immunodetection

The monoclonal or monospecific antibodies of the previous example are used as probes in known immunohistological techniques in order to identify the physical distribution of PASA-comprising proteins in normal and arthritic mice, and in larger animals (e.g., sheep, dogs, cows, horses, etc.) from which sufficient material for protein purification is more readily obtained, according to standard methods. If necessary, animals at various stages of development are so examined. Ausubel, F. M., et al., Eds., Current Protocols in Molecular Biology, Vol. 2, Greene Publishing Associates and John Wiley & Sons, pages 14.0.1–14.6.13 (1993).

Tissues having relatively high concentrations of PASA-comprising proteins are removed from animals post-mortem and used as a source of PASA-comprising proteins for purification thereof. As a purification assay, the activation of R28 cells, described in a previous example, is used. Standard methods of protein purification are used. Lehninger, A. L., Biochemistry, 2d Ed., pp.95–121. Additionally or alternatively, affinity columns comprising as binding agents the monoclonal or monospecific antibodies of the previous example are used. Harlow, E., and Lane, D., Antibodies: A Laboratory Manual, Cold Spring Harbor Laboratories, Cold Spring Harbor, N.Y., pages 511–552 (1988). The purified PASA-comprising proteins are sequenced by standard methods, including but not limited to partial proteolysis and repetitive Edman degradation. Lehninger, A. L., Biochemistry, 2d Ed., pp.95–121 (1978).

DNA Sequences Encoding PASA-Comprising Proteins

The amino acid sequence of PASA-derived oligopeptides bound to APCs, or of PASA-comprising proteins, or both, are used in conjunction with the genetic code (Table 2) to design corresponding DNA sequences for the construction of synthetic oligonucleotides capable of specifically hybridizing to genes encoding PASA-comprising proteins. Lathe, R., J. Mol. Biol. 183: 1–12 (1985). The oligonucleotides are used as probes to detect DNA restriction fragments that encode PASA-comprising protein amino acid sequences; the restriction fragments are then cloned into appropriate vectors. Ruter, W. J., et al., U.S. Pat. No. 4,440,859 (Apr. 3, 1984). Alternatively, the oligonucleotides are used as primers in PCR reactions to amplify DNA sequences encoding PASA-comprising proteins. Mullis, K. B., et al., U.S. Pat. No. 4,965,188 (Oct. 23, 1990). In particular, inverse PCR is used to generate the maximum amount of PASA-comprising protein coding sequence information from the least amount of amino acid sequence information. Ochman, H., et al., in PCR Technology: Principles and Applications for DNA Amplification, Erlich, H. A., ed., Stockton Press, London, pages 105–111 (1989). The PCR products are then cloned into appropriate vectors and sequenced or sequenced directly. Gyllensten, U., in PCR Technology: Principles and Applications for DNA Amplification, Erlich, H. A., ed., Stockton Press, London, pages 45–60 (1989). To produce PASA-comprising proteins, DNA sequences encoding the proteins are cloned into appropriate expression vectors which are then introduced into their cognate host cells, wherein the directed biosynthesis of PASA-comprising proteins occurs. Rutter, W. J., et al., U.S. Pat. No. 4,440,859 (Apr. 3, 1984).

Example 8

Therapeutic Compositions

The PASA-comprising proteins of the previous example, and the variable regions of the TCR subunits of the transgene of the invention, are used to generate several compositions useful in treating arthritic animals including humans.

Immunization with TCR Oligopeptides

Although the mechanism remains unclear, immunization with synthetic oligopeptides corresponding to variable regions of TCR subunits has been demonstrated to prevent or reverse experimental allergic encephalomyelitis (EAE). EAE is induced by autoimmunization of animals with MBP and produces the clinical symptoms of MS, i.e., demyelination and paralysis. Howell, W. M., et al., Science 246: 668–670 (1989); Vanderbark et al., Nature 341: 541–544 (1989). A pilot trial of treatment of humans suffering from MS with TCR-derived oligopeptides is currently underway. Oksenberg, J. R., et al., J. Neurol. Sci. 115(Suppl.): S29–S37 (1993).

Although the TCR variable region amino acid sequences of the invention are isolated from a murine hybridoma, the remarkable relatedness of TCRs involved in autoimmune diseases crosses species lines, suggesting that the molecular components of the immune system are sufficiently conserved so as to allow human therapeutic compositions to be derived from murine TCR molecules. For example, some MS patients have TCR populations that are over-represented by TCRs that recognize a fragment of myelin basic protein (MBP) bound to a part of the HLA receptor (the HLA-DR2 molecule). A sequence of three amino acids, apparently required to recognize the MBP: HLA-DR2 complex, was present in these TCRs. Oksenberg, J. R., et al., *Nature* 362: 68–70 (1993). The same fragment of MBP is recognized by a prevalent class of TCRs in an animal model of MS, EAE. The TCRs that are prevalent in EAE animals have the same sequence of three amino acids found in TCRs in MS humans. Gold, D. P., et al., *J. Exp. Med.* 174: 1467–1476 (1991); Hashim, G., et al., *J. Immunol.* 146: 515–520 (1991); Offner, H., et al., *J. Immunol.* 146: 4165–4172 (1991); Vainiene, M., et al., *J. Neurosci. Res.* 31: 413–420 (1992); Offner, H., et al., *J. Immunol.* 148: 1706–1711 (1992); Gold, D. P., et al., *J. Immunol.* 148: 1712–1717 (1992); Offner, H., et al., *J. Immunol.* 151: 506–517 (1993).

The amino acid sequences of the variable regions of the TCR subunits derived from R28 [SEQ ID Nos. 5 and 7] are used to design synthetic oligopeptides having therapeutic value in non-murine animals including humans. Oligopeptides comprising amino acid sequences derived from SEQ ID NOs. 5 and 7 are chemically synthesized according to standard methods (Stewart and Young, *Solid Phase Peptide Synthesis*, Pierce Chemical Co., Rockland, Ill. (1985)) and purified from reaction mixtures by reversed phase HPLC. The most effective anti-arthritic oligopeptides are identified by the assays described in Example 4.

Oral Tolerance Therapy

Although autoimmunization can result from direct presentation of a self-antigen to an animal, e.g., by subcutaneous injection, tolerance can be achieved by presenting antigens to an animal by oral ingestion. This process, called oral tolerance therapy, appears to activate T cells that secrete cytokines that counter some of the autoimmune response's effects. Strobel, S., et al., *Immunology* 56: 577–564 (1985); Mowat, A. M., *Immunology* 56: 253–260 (1985); Mowat, A. M., et al., *Adv. Exp. Med. Biol.* 216A: 709–720 (1987); Lamont, A. G., et al., *Immunology* 63: 737–739 (1988); Mowat, A. M., et al., *Immunology* 64: 141–145 (1988). An antigen presented by oral ingestion that results in enhanced tolerance of the antigen is called a tolerogen. Thompson, H. S., et al., *Clin. Exp. Immunol.* 72: 20–25 (1988); Thompson, H. S. G., and Staines, N. A., *Clin. Exp. Immunol.* 64: 581–586 (1985); Thompson, H. S., and Staines, N. A., *Immunol. Today* 11: 396–399 (1991).

Oral tolerance therapy for autoimmune disease was first demonstrated by feeding myelin basic protein to EAE animals. Bitar, D. M., and Whitacre, C. C., *Cell Immunol.* 112: 364–370 (1988); Fuller, K. A., et al., *J. Neuroimmunol.* 28: 15–26 (1990); Whitacre, C. C., et al., *J. Immunol.* 147: 2155–2163 (1991). Oral tolerance therapy has been demonstrated to be effective in suppressing arthritis in animal models, particularly collagen-induced arthritis (CIA). Thomspon, H. S., and Staines, N. A., *Clin. Exp. Immunol.* 64: 581–586 (1986); Nagler-Anderson, C., et al., *Proc. Natl. Acad. Sci. (USA)* 83: 7443–7446 (1986). Synthetic oligopeptides, derived from the amino acid sequence of type II collagen, are also effective as tolerogens. Myers, L. K., et al., *J. Exp. Med.* 170: 1999–2010 (1989). Synthetic polypeptidic tolerogens can be manipulated to further define the eptiope(s) required for tolerogenicity. Meyers, L. K., et al., *J. Immunol.* 149: 1439–1443 (1992); Meyers, L. K., et al., *J. Immunol.* 150: 4652–4658 (1993); Myers, L. K., et al., *J. Immunol.* 151: 500–505 (1993).

The amino acid sequences of oligopeptides bound to APCs in the transgenic arthritic mice of the invention, or of PASA-comprising proteins, are used to design the sequences of synthetic oligopeptides for oral tolerance therapy. For human therapy, amino acid sequences from human PASA-comprising proteins are preferably used. Oligopeptides comprising amino acid sequences of choice are chemically synthesized according to standard methods (Stewart and Young, *Solid Phase Peptide Synthesis*, Pierce Chemical Co., Rockland, Ill. (1985)) and purified from reaction mixtures by reversed phase HPLC. The most effective anti-arthritic oligopeptides are identified by the assays described in Example 4, using oral ingestion as the means of administering the oligopeptides to the arthritic animals.

MHC Antagonists

In EAE, in vivo competition between the artificially-introduced "self" antigen and synthetic oligopeptides derived therefrom can be used to modulate the induction of autoimmune responses. These MHC antagonists are apparently bound by MHC molecules of APCs and presented to T cells but, because of chemical changes from the original antigen, are not sufficiently stimulatory to T cells so as to activate them. Zamvil, S. S., and Steinman, L., *Annu. Rev. Immunol.* 8: 579–621 (1990); Steinman, L., *Adv. Immunol.* 49: 357–379. The activation of T cells responsible for subsequent immunologic events that culminate in arthritis is delayed or inhibited, with a parallel effect on the course of the disease.

The amino acid sequences of oligopeptides bound to APCs in the transgenic arthritic mice of the invention, or of PASA-comprising proteins, are used to design the sequences of synthetic oligopeptides that serve as MHC antagonists. For human therapy, amino acid sequences from human PASA-comprising proteins are preferably used. Oligopeptides comprising amino acid sequences of choice are chemically synthesized according to standard methods (Stewart and Young, *Solid Phase Peptide Synthesis*, Pierce Chemical Co., Rockland, Ill. (1985)) and purified from reaction mixtures by reversed phase HPLC. The most effective anti-arthritic oligopeptides are identified by the assays described in Example 4.

Utility of the Invention

The embodiments of the invention described above can be used for such purposes as listed below, alone or in combination with each other or other complementary methods and/or compositions.

(1) Potential anti-arthritic therapeutic compositions are evaluated for their efficacy by determining the effect of the compositions on the temporal and/or histological progress of arthritis in transgenic arthritic mice. Potential anti-arthritic therapeutic compositions that are evaluated include, but are not limited to, chemical compounds, tolerogens, anti-inflammatory agents, genetic therapy agents, and genetically engineered microorganisms or cells. See Example 4 for details.

(2) Potential arthritogenic (arthritis-inducing) compositions are evaluated for their hazardousness by determining the effect of the compositions on the temporal and/or histological progress of arthritis in transgenic arthritic mice, or by determining their ability to enhance penetrance of the KRN transgenic allele in non-arthritic KRN transgenic mice. Potential arthritogenic compositions that are evaluated include, but are not limited to, chemical compounds, tolerogens, anti-inflammatory agents, genetic therapy agents, and genetically engineered microorganisms or cells. See Example 5 for details.

(3) B or T cells from arthritic transgenic mice are isolated and fused to immortalizing cells to generate B cell hybridomas that produce monoclonal antibodies that recognize an endogenous polypeptide arthritogenic self antigen (PASA), or T cell hybridomas that are activated by presentation thereto of PASA-comprising proteins. The hybridomas monoclonal antibodies are used (a) to evaluate individual animals including humans for their risk of developing rheumatoid arthritis and/or (b) to isolate PASA-comprising proteins from animals including humans. See Example 6 for details.

(4) Antigen-presenting cells (APCs) from transgenic arthritic mice are prepared en masse and polypeptide antigens associated therewith are isolated. Because of the limited TCR repertoire in the transgenic arthritic mice, most T cells are directed to endogenous polypeptide arthritogenic self antigens. Monoclonal or Monospecific antibodies that recognize the APC-associated antigens are prepared and used to isolate PASA-comprising proteins from animals including humans. Additionally or alternatively, the amino acid sequences of APC-associated peptides are determined and are used to design oligonucleotide probes and/or primers that are used to isolate genes encoding PASA-comprising proteins, which are used to produce PASA-comprising proteins via recombinant DNA technology. See Examples 6 and 7 for details.

(5) Compositions, particularly synthetic oligopeptides, useful in anti-arthritic therapy, including oral tolerance therapy, in animals including humans, are derivable from the amino acid sequences of (a) isolated PASA-comprising proteins of the invention or (b) the variable regions of the TCR subunits of the invention [SEQ ID NOs. 5 and 7]. See Example 8 for details.

What is claimed is:

1. A transgenic mouse whose somatic and germ line cells contain a transgene encoding a T-cell receptor (TCR), wherein said TCR has an alpha-subunit comprising a variable region having an amino acid sequence as shown in SEQ ID NO.5 and a beta subunit comprising a variable region having an amino acid sequence as shown in SEQ ID NO.7, wherein the expression of said transgene results in said mouse having chronic inflammation and deformation of one or more synovial joints.

2. The mouse of claim 1, wherein said t-cells contain a first transgene having a nucleotide sequence selected from SEQ ID NO. 2 Or SEQ ID NO. 4 and a second transgene having a nucleotide sequence selected from SEQ ID NO. 3 or SEQ ID NO. 6.

3. The mouse of claim 2, wherein said nucleotide sequence of said first transgene is shown in SEQ ID NO. 2.

4. The mouse of claim 2, wherein said nucleotide sequence of said first transgene is shown in SEQ ID NO. 4.

5. The mouse of claim 2, wherein said nucleotide sequence of said second transgene is shown in SEQ ID NO. 3.

6. The mouse of claim 2, wherein said nucleotide sequence of said second transgene is shown in SEQ ID NO. 6.

7. The mouse of claim 1, which is a mouse of the NOD strain.

8. A method for determining the anti-arthritic potential of a composition comprising the steps of:
   (a) administering a known dose of said composition to a first transgenic mouse before inflammation, irremediable joint destruction and limb deformation have occurred;
   (b) detecting the onset of irremediable joint destruction and limb deformation in said first transgenic mouse; and
   (c) comparing the time of onset of irremediable joint destruction and limb deformation in said first transgenic mouse to the time of onset of irremediable joint destruction and limb deformation in a second transgenic arthritic mouse which has not been exposed to said composition,
wherein said first transgenic mouse and said second transgenic mouse both contain and express a transgene encoding a T-cell receptor (TCR), wherein said TCR has an alpha-subunit comprising a variable region having an amino acid sequence as shown in SEQ ID NO.5 and a beta-subunit comprising a variable region having an amino acid sequence as shown in SEQ ID NO.7 and wherein expression of said transgene results in a statistically significant delay in the time of onset of irremediable joint destruction and limb deformation in said first transgenic mouse relative to the time of onset of irremediable joint destruction and limb deformation in said second transgenic arthritic mouse indicates the anti-arthritic potential of said composition.

9. A method for determining the anti-arthritic potential of a composition comprising the steps of:
   (a) administering a known dose of said composition to a first transgenic mouse before irremediable joint destruction and limb deformation has occurred;
   (b) monitoring the extent of irremediable joint destruction and limb deformation in said first transgenic mouse; and
   (c) comparing the extent of irremediable joint destruction and limb deformation in said first transgenic mouse to the extent of irremediable joint destruction and limb deformation in a second transgenic mouse which has not been exposed to said composition,
wherein said first transgenic mouse and said second transgenic mouse both contain and express a transgene encoding a T-cell receptor (TCR), wherein said TCR has an alpha-subunit comprising a variable region having an amino acid sequence as shown in SEQ ID NO.5 and a beta-subunit comprising a variable region having an amino acid sequence as shown in SEQ ID NO.7 and wherein expression of said transgene results in a statistically significant decrease in the extent of irremediable joint destruction and limb deformation in said first transgenic arthritic mouse relative to the extent of irremediable joint destruction and limb deformation in said second transgenic mouse indicates the anti-arthritic potential of said composition.

10. A method for determining the arthritogenic potential of composition comprising the steps of:
   (a) administering a known dose of said composition to a first KRN transgenic mouse before irremediable joint destruction and limb deformation has occurred;
   (b) detecting the onset of irremediable joint destruction and limb deformation in said first KRN transgenic mouse; and (c) comparing the time of onset of irremediable joint destruction and limb deformation in said first KRN transgenic mouse to the time of onset of irremediable joint destruction and limb deformation in a second KRN transgenic mouse which has not been exposed to said composition, wherein said first transgenic mouse and said second transgenic mouse both contain and express a transgene encoding a T-cell receptor (TCR), wherein said TCR has an alpha-subunit comprising a variable region having an amino acid sequence as shown in SEQ ID NO.5 and a beta-subunit comprising a variable region having an amino acid sequence as shown in SEQ ID NO.7 and wherein expression of said transgene results in a statistically significant delay in the time of onset of irremediable joint destruction and limb deformation in said second KRN transgenic mouse relative to the time of onset of irremediable joint destruction and limb deformation in said first KRN transgenic mouse indicates the arthritogenic potential of composition.

11. A method for determining the arthritogenic potential of a composition comprising the steps of:

(a) administering a known dose of said composition to a first KRN transgenic mouse before irremediable joint destruction and limb deformation has occurred;

(b) monitoring the extent of irremediable joint destruction and limb deformation in said first KRN transgenic mouse; and (c) comparing the extent of irremediable joint destruction and limb deformation in said first KRN transgenic mouse to the extent of irremediable destruction and limb deformation in a second KRN transgenic mouse which has been exposed to said composition, wherein said first transgenic mouse and said second transgenic mouse both contain and express a transgene encoding a T-cell receptor (TCR), wherein said TCR has an alpha-subunit comprising a variable region having an amino acid sequence as shown in SEQ ID NO.5 and a beta-subunit comprising a variable region having an amino acid sequence as shown in SEQ ID NO.7 and wherein a statistically significant increase in the extent of irremediable joint destruction and limb deformation in said first KRN transgenic mouse relative to the extent of irremediable joint destruction and limb deformation in said second KRN transgenic mouse indicates the arthritogenic potential of said composition.

12. The method of any one of claims 8–11, wherein said composition comprises a chemical compound administered by circulatory injection or oral ingestion.

13. The method of any one of claims 8–11, wherein said composition comprises a polypeptide administered by circulatory injection of an isolated or recombinant bacterium or virus that is live or attenuated, wherein said polypeptide is present on the surface of said bacterium or virus prior to injection.

14. The method of any one of claims 8–11, wherein said composition comprises a polypeptide administered by circulatory injection of an isolated or recombinant bacterium or virus which reproduces within said mice, and said polypeptide is produced within said mouse by genetic expression of a DNA sequence encoding said polypeptide.

15. The method of any one of claims 8–11, wherein said composition is selected from the group consisting of a prospectively anti-inflammatory composition, an actively anti-inflammatory composition, and a composition that has no effect on inflammation per se but limits the destruction of tissue resulting from inflammatory events.

16. The method of claim 10 or 11, wherein said first KRN transgenic mouse is a KRN-transgenic NOD mouse and said second KRN transgenic mouse is a KRN-transgenic NOD mouse.

17. The method of any one of claims 8–11, wherein said t-cells contain a first transgene having a nucleotide sequence selected from SEQ D NO. 2 or SEQ ID NO. 4 and a second transgene having a nucleotide sequence selected from SEQ ID NO. 3 or SEQ ID NO. 6.

* * * * *

UNITED STATES PATENT AND TRADEMARK OFFICE
CERTIFICATE OF CORRECTION

PATENT NO. : 5,675,060

DATED : October 7, 1997

INVENTORS : Benoist *et al.*

It is certified that an error appears in the above-identified patent and that said Letters Patent is hereby corrected as shown below.

On the title page, item [73], after "Scientifique", insert --, both of Paris, France"; and after "Strasbourg 1,", delete "all of Paris, France" and insert therein --Strasbourg, France--.

Claim 2, in column 43, line 33, replace "t-cells" with --cells; and line 35, replace "Or" with --or--.

Claim 8, part (c), in column 43, line 63, after "second transgenic" delete "arthritic".

Claim 8, in column 44, line 32, after "second transgenic" delete "arthritic".

Claim 9, in column 44, line 56, before "mouse relative to the extent" delete "arthritic".

Claim 10, in column 45, line 19, after "arthritogenic potential of" insert --said--.

Claim 11, part (c), in column 45, line 30, after "extent of irremediable" insert --joint--; and line 32, after "which has" insert --not--.

Claim 17, in column 46, line 34, replace "t-cells" with --cells--; and line 35, replace "SEQ D NO. 2" with --SEQ ID NO. 2--.

Signed and Sealed this

Eleventh Day of January, 2000

Attest:

Q. TODD DICKINSON

*Attesting Officer*     *Acting Commissioner of Patents and Trademarks*